United States Patent [19]

Rosenthal et al.

[11] Patent Number: 5,086,229

[45] Date of Patent: * Feb. 4, 1992

[54] NON-INVASIVE MEASUREMENT OF BLOOD GLUCOSE

[75] Inventors: Robert D. Rosenthal, Gaithersburg; Lynn N. Paynter, Elkridge; Linda H. Mackie, Rockville, all of Md.

[73] Assignee: Futrex, Inc., Gaithersburg, Md.

[*] Notice: The portion of the term of this patent subsequent to Jul. 2, 1991 has been disclaimed.

[21] Appl. No.: 544,580

[22] Filed: Jun. 27, 1990

Related U.S. Application Data

[63] Continuation-in-part of Ser. No. 298,904, Jan. 19, 1989.

[51] Int. Cl.$^5$ .................. G01N 33/50; G01N /21/59
[52] U.S. Cl. ...................... 250/341; 250/339
[58] Field of Search .............. 250/339, 341, 343; 356/39; 128/633

[56] References Cited

U.S. PATENT DOCUMENTS 4,882,492  11/1989  Koashi et al. .................. 250/341
4,883,953  11/1989  Schlager ......................... 250/341

Primary Examiner—Janice A. Howell
Assistant Examiner—Richard Hanig
Attorney, Agent, or Firm—Rothwell, Figg, Ernst & Kurz

[57] ABSTRACT

Near-infrared quantitative analysis instruments and methods non-invasively measure blood glucose by analyzing near-infrared energy following interactance with venous or arterial blood, or transmisison through a blood containing body part. The instruments and methods are accurate and readily lend themselves to at-home testing by diabetics.

43 Claims, 18 Drawing Sheets

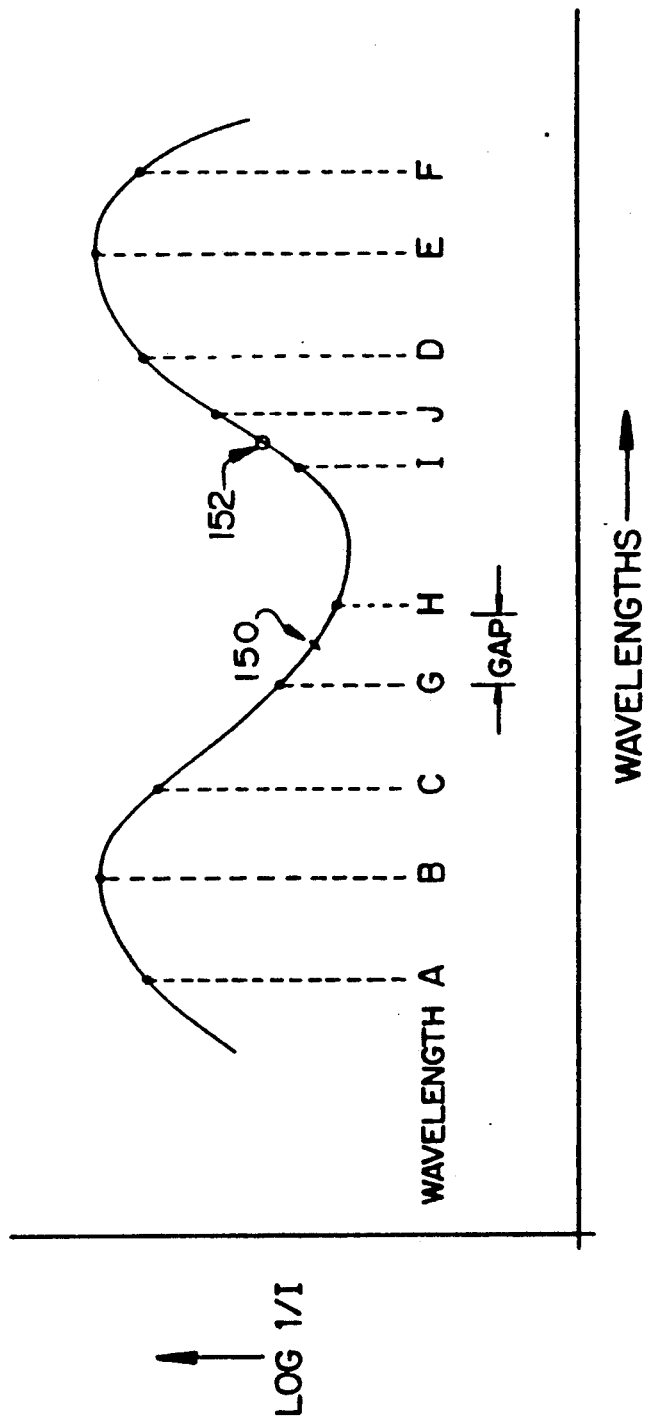

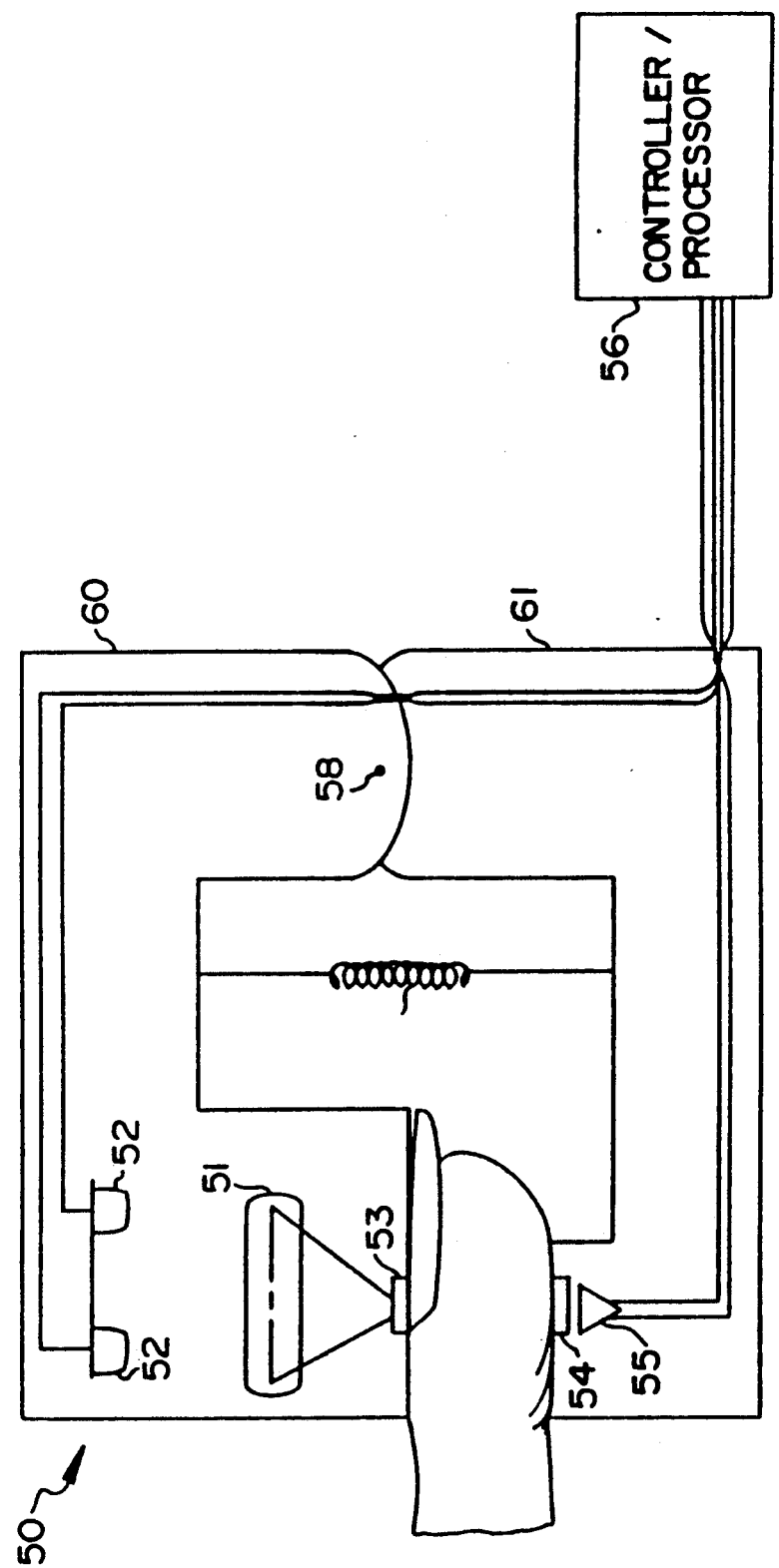

NON-INVASIVE MEASUREMENT OF BLOOD GLUCOSE

CROSS-REFERENCE TO RELATED APPLICATION

This application is a continuation-in-part of copending application Ser. No. 07/298,904, filed Jan. 19, 1989.

BACKGROUND OF THE INVENTION

1. Field of the Invention

This invention relates to instruments and methods for the non-invasive quantitative measurement of blood glucose.

2. Description of Background Art

Information concerning the chemical composition of blood is widely used to assess the health characteristics of both people and animals. For example, analysis of the glucose content of blood provides an indication of the current status of metabolism. Blood analysis, by the detection of above or below normal levels of various substances, also provides a direct indication of the presence of certain types of diseases and dysfunctions.

The normal method of determining blood chemistry is by removing a sample of blood (e.g. 5-10 ml) and performing one or more standard chemical tests. These types of tests are moderately expensive, require one class of trained technicians to remove the blood and another class of trained technicians to perform the chemical tests. Moreover, the results of the blood tests often are not available for several hours, and sometimes even several days.

Recently, an alternative type of technology (i.e. self-contained instruments) has been introduced for relatively rapid blood screening of a large number of subjects. These instruments, in general, use a much smaller blood sample (approximately 0.25 ml) from a "finger poke." This small blood sample is placed on a chemically-treated carrier and entered into the instrument. These instruments normally provide either an individual analyses (e.g. glucose level) or multiple analysis in a few moments. These types of instruments unfortunately are quite costly, e.g., in the range of several thousand dollars.

A third class of blood instrumentation is available for the specific purpose of determining glucose level in people with diabetes. This technology also uses a small sample from a finger poke and the sample is placed on a chemically treated carrier which is inserted into a portable battery operated instrument. In general, these instruments provide a single function; i.e. measurement of glucose. Although these specialized instruments are relatively low cost ($300 or less is typical), the cost of the disposable carrier "stick" must be considered. Since some diabetic patients may require glucose analysis four or more times a day, the cost over a period of a year can become significant.

Current glucose analytical systems require blood to be extracted from the body prior to performing the analysis. This blood withdrawal requirement limits the application of such testing; many people who may be interested in knowing their glucose level are reluctant to have either their finger poked or blood samples removed by hypodermic needle. This reluctance or anxiety in allowing blood sample removal is due to concern over the possibility of infection, discomfort (pain) and generalized patient fear.

Thus, there is a great need for non-invasive analytical instruments and methods that would provide essentially the same accuracy as conventional blood glucose tests. Moreover, there is a need for a non-invasive low-cost method for measurement of glucose in diabetic patients.

Near-infrared (sometimes referred to herein as simply "near-IR") quantitative analysis is widely used in the field of agriculture for determining chemical compositions within grain, oilseeds, and other agricultural products. As an example, near-IR energy reflected from the surface of finely ground seeds and grain provides information concerning protein and moisture content. For a general introduction to near infrared quantitative analysis, see "An Introduction to Near-Infrared Quantitative Analysis" presented by Robert D. Rosenthal at the 1977 Annual Meeting of American Association of Cereal Chemists. Near-infrared technology has been extended to allow totally non-destructive measurements by using light transmission through a sample as discussed in "Characteristics of Non-Destructive Near-Infrared Instruments for Grain and Food Products" by Robert D. Rosenthal, presented at the 1986 Meeting at the Japan Food Science Institute. Although this transmission approach avoids the need to finely grind the sample, it is not suited for use where access to two opposite surfaces is not available.

One example of this transmission approach is provided in U.S. Pat. No. 4,621,643 (New, Jr. et al., 1986) relates to an optical oximeter apparatus for determining pulse rate and degree of arterial oxygen saturation. Light energy is passed through an appendage of the body, e.g. a finger, and strikes a detector positioned on a side of the appendage opposite from the light source. Pulse rate and saturated oxygen are calculated from coefficients of extinction of light at the selected wavelengths.

Another approach to near-infrared quantitative analysis, using near-infrared interactance, was developed for non-invasively measuring body fat content. This approach is described in "A New Approach for the Estimation of Body Composition: Infrared Interactance", Joan M. Conway et al., The American Journal of Clinical Nutrition, 40: Dec. 1984, pages 1123-1230. In this non-invasive technique, a small optical probe that allows optical energy to enter the arm is placed on the biceps. The percent body fat of the entire body is determined by measuring the spectrum change of the energy returned from an area adjacent the light entry point.

SUMMARY OF THE INVENTION

In accordance with the present invention, a near-infrared quantitative analysis instrument for measuring blood glucose comprises means for introducing near-IR energy into blood present in a body part of a subject, means for detecting near-IR energy emerging from the subject, means for converting an electrical signal corresponding to the detected energy into a readout indicative of the quantity of glucose present in the blood of the subject, and means for positioning the introducing means and detecting means adjacent to the body part of the subject.

The present invention also provides methods for the near-infrared quantitative analysis of blood glucose, these methods including the steps of introducing near-IR energy into the blood within a body part of a subject, detecting near-IR energy emerging from the subject, the detector providing an electrical signal upon detecting said emerged energy, and processing the electrical signal to provide a second signal indicative of the amount of glucose present in the blood. Some of these inventive methods utilize the principal of near-IR transmission while others utilize the principal of near-IR interactance.

In accordance with one aspect of the present invention, a near-infrared quantitative analysis instrument for measuring blood glucose comprises means for introducing near-IR energy into blood present in a blood vessel, means for detecting near-IR energy following interactance of the same with the blood, and means for positioning the introducing means and detecting means over a blood vessel of the subject.

This aspect of the invention further relates to methods wherein near-IR energy is introduced into a vein or artery of a subject and interacts with blood glucose, the near-IR energy emerging from the subject is detected by a detector which provides an electrical signal, and the signal is processed to provide a readout indicative of the amount of glucose in the blood.

This aspect of the invention also relates to means and methods for marking a position over a vein or artery of a subject and then aligning a near-IR analysis instrument with the markings to accurately position the instrument.

Another aspect of the invention relates to an apparatus for measuring blood glucose via near-IR transmission through a blood-containing body part, the apparatus including mean for introducing near-IR energy into one side of a body part, means for detecting near-IR energy emerging from an opposite side of the body part and means for positioning the near-IR introducing and detecting means on opposite sides of the body part.

This aspect of the invention also relates to methods for measuring blood glucose via near-IR transmission including the steps of introducing near-IR energy into one side of a blood-containing body part, detecting near-IR energy emerging from an opposite side of the body part and calculating blood glucose content.

BRIEF DESCRIPTION OF THE DRAWINGS

FIG. 6 is a plot of log (1/I) versus wavelength.

FIG. 19 illustrates a non-invasive glucose measurement instrument according to one embodiment of the present invention;

DETAILED DESCRIPTION OF THE PREFERRED EMBODIMENTS

Figure 1:
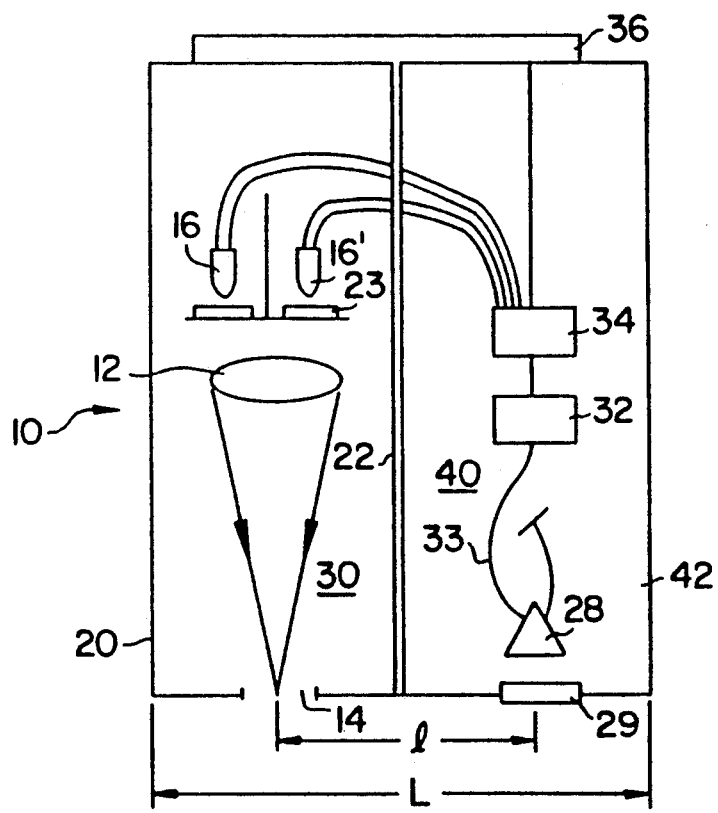
FIG. 1 is a partially schematic elevational view of a near-infrared quantitative blood analysis instrument to which the present invention pertains.

In accordance with one embodiment, the invention uses the principle of light interactance to measure blood glucose level non-invasively by locating an optical transmitter and a detector on the skin surface near either an artery or vein. Alternatively, the invention uses the principal of light transmission through a portion of the body that has relatively uniform profusion of blood in order to measure non-invasively blood glucose.

In general, the arteries and veins of the human body are buried deep in the body to protect them from possible harm. However, in certain locations of the body, these blood carrying vessels are close to the skin surface. This is particularly true for veins. Some examples of such locations are at the crease of the elbow, the wrist, the back of the hand, and the bridge of the nose. Since the concentration of glucose is relatively constant in both the veins and arteries, valid measurements can be obtained in either. However, because veins are generally closer to the skin's surface, they usually are the better candidate for non-invasive measurements.

The finger tip is another site particularly well suited for performing blood measurements with near-IR light. The blood supply is distributed within the finger tip and, thus, small variations in the placement of a near-IR emitter or detector will not have a profound effect on the measurement results.

According to one embodiment of the invention utilizing near-IR interactance analysis techniques, near-IR light energy at bandwidths centering on one or more wavelengths of interest is passed through the skin and connective tissues and into a blood vessel of a subject. A portion of the energy re-emerges from the blood vessel of the test subject and is detected by a detector. Following amplification of the detector-generated signal, the amplified output is processed into an output signal indicating the amount of glucose in the subject's blood. The output signal drives a display device for providing a visual display of blood glucose content.

According to another embodiment of the invention utilizing near-IR transmission analysis techniques, near-IR light energy at bandwidths centering on one or more wavelengths of interest is transmitted through a blood-containing portion of the body of a test subject. The near-IR energy emerges from the test subject, generally opposite from the near-IR source, and is detected by a detector. Following amplification of the detector-generated signal, the amplified output is processed into an output signal indicating the amount of glucose in the subject's blood.

In one embodiment utilizing near-IR interactance, the entire analytical instrument, including near-infrared source, transmitter, detector, amplifier, data processing circuitry and readout is contained within a lightweight hand-held unit. See FIG. 1. Infrared emitting diodes (IREDs) disposed in one chamber of the unit are focused to transmit near-IR energy of preselected wavelength(s) to, e.g., a prominent vein of the wrist. The near-IR energy interacts with the constituents of the venous blood and is re-emitted from the vein. A detector housed within a second chamber of the unit is disposed along the vein a distance (1) from the emitter and collects this energy. The detected signal is amplified and data processed into a signal indicative of the amount of glucose in the blood. This signal is then fed to a readout device (preferably a digital readout) for recordation by a technician or direct analysis by a physician or the subject himself.

Other near-IR apparatus, such as the optical probe and associated instrumentation described in Rosenthal U.S. Pat. No. 4,633,087, are useful in the practice of the present methods in which near-IR interactance is used to quantitatively measure blood glucose levels.

This embodiment can utilize a location device specially adapted to permit the user to locate the interactance instrument discussed above accurately along a vein. The location device permits the skin to be marked to ensure that repeated measurements are taken from the same location.

In the lightweight, hand-held interactance analysis instrument 10 illustrated in FIG. 1, included is one or more means for providing at least one point source of near-infrared energy of a predetermined bandwidth of interest which is positioned within a first chamber 30 of the instrument 10. The near-infrared point source means is positioned so that near-infrared energy being emitted from the point source means will be focussed by lens 12 through window 14 and onto the skin of the test subject. The near-infrared point source means may comprise one or a plurality of infrared emitting diodes (IREDs). Two such IREDs 16 are visible in the embodiment illustrated in FIG. 1. In other embodiments employing a plurality of IREDs, three, four or more IREDs may be utilized as the point source means.

Figure 5A:
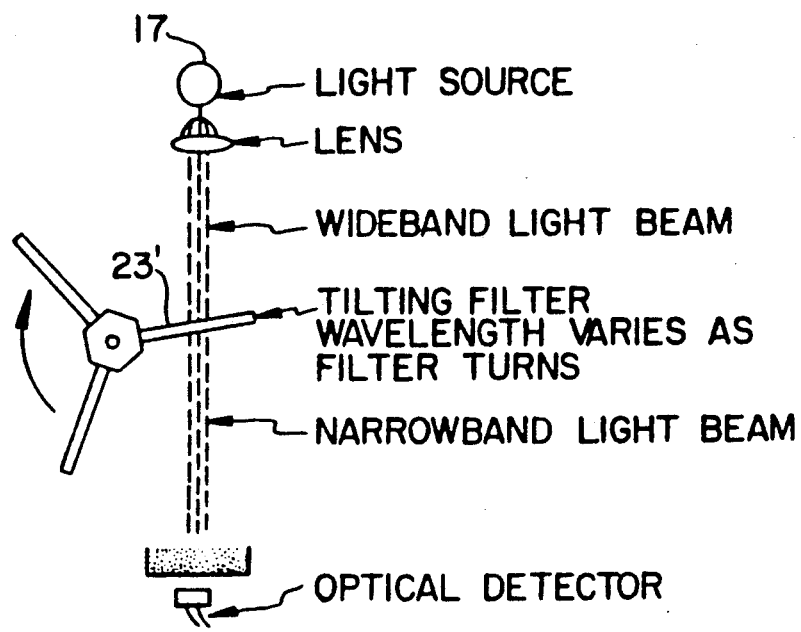
FIGS. 5A and 5B illustrate two known configurations for interposing filters in a light path.
Figure 5B:
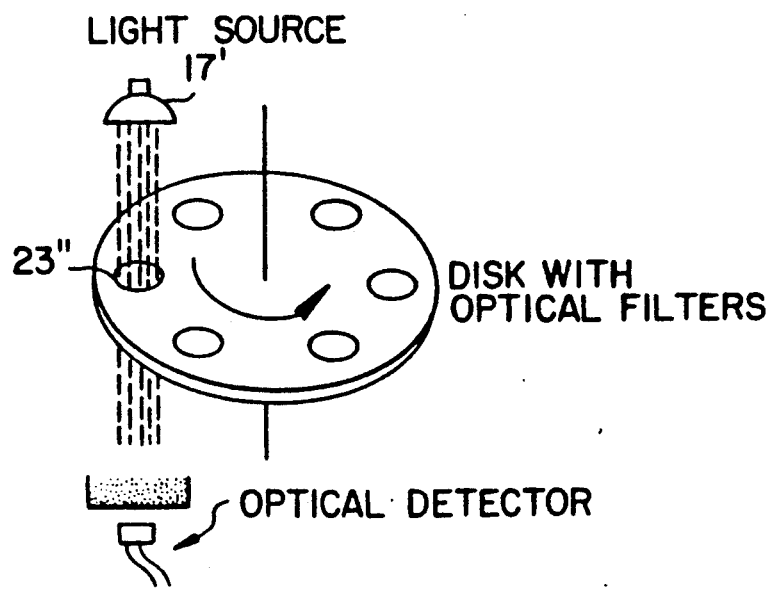

In lieu of laborious characterization and sorting of each IRED, narrow bandpass optical filters (as shown schematically in FIG. 1) can be provided between the infrared emitting diodes and the lens 12. According to this embodiment, a filter 23 is positioned between each IRED and lens 12 for filtering near infrared radiation exiting each IRED and thereby allowing a narrow band of near-infrared radiation of predetermined wavelength to pass through the filter and lens 12. Utilization of narrow bandpass optical filters provides for specific wavelength selection independent of the center wavelengths of the particular infrared emitting diodes being used. Measurements can be taken inside the half power bandwidth of the IREDs, or alternatively, outside the half power bandwidth of the IREDs as disclosed in U.S. Pat. No. 4,286,327. FIGS. 5A and 5B illustrate two other known configurations for interposing filters 23' and 23" respectively in a light path. The light source in FIGS. 5A and 5B can be either a light bulb 17 or 17' respectively or one or more IREDs.

An optical detector, illustrated schematically FIG. 1 and designated by reference numeral 28, is disposed within a lower end portion 42 of a second chamber 40 in case 20. Inner wall 22 is positioned between detector 28 and illumination section 30, thereby providing an optically-isolating mask which prevents near infrared radiation from the point source means and/or lens 12 from impinging directly on detector 28. A near-infrared optical detector 28 generates an electrical signal when near-infrared radiation is detected thereby.

The optical detector 28 is connected to the input of an electrical signal amplifier 32 by suitable electrical conducting means 33. Amplifier 32 may be an inexpensive integrated circuit (IC) signal amplifier, and amplifies the signals generated when near-IR energy strikes detector 28. The output of amplifier 32 is fed to a controller/data processor and display driver 34 which provides a signal to readout device 36. The readout device 36 may have a digital display for directly displaying the amount of glucose present in the subject's blood.

The embodiment of FIG. 1 includes an optical filter 29 for shielding all but the desired near-IR energy from detector 28. Filter 29 and window 14 are positioned for direct contact with the skin of the test subject. An optically clear window can be employed in lieu of filter 29, if desired and in lieu of the window opening 14.

As noted earlier, the embodiment illustrated in FIG. 1 utilizes the principal of near-IR interactance for quantitative analysis. In interactance, light from a source is shielded by an opaque member from a detector so that only light that has interacted with the subject is detected.

In use, the analysis instrument 10 is positioned so that its flat bottom surface rests on the skin directly above the prominent vein of the wrist of a test subject. Light at the selected wavelengths emerging from the instrument interacts with venous blood of the subject and is detected by detector 28. Detector 28 generates an electrical signal which is processed as described above.

Figure 3:
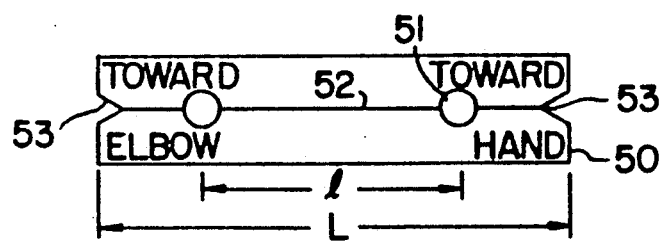
FIG. 3 is an elevational view of a location device for use with the instrument shown in FIG. 1.

Accurate analysis is facilitated when the user locates the transmitter and detector filter (or window) directly over the prominent vein of the wrist. The location device illustrated in FIG. 3 simplifies this procedure. The device 50 is constructed of, e.g., a plastic material and has an overall length L equal to the length L of the analysis instrument 10 of FIG. 1. Two holes 51 are present in the device and are located in the same relation as 14 and 29 in FIG. 1, on midline 52, a distance l apart corresponding to the distance l of FIG. 1. The holes 51 permit observation of the prominent vein. When the device is placed on the wrist and the vein is centered in each hole 51, the wrist is marked (e.g. with a felt-tipped pen) at notches 53. The location device is then removed and replaced by the analysis instrument 10 with assurance that the instrument is properly located over the vein.

Figure 4:
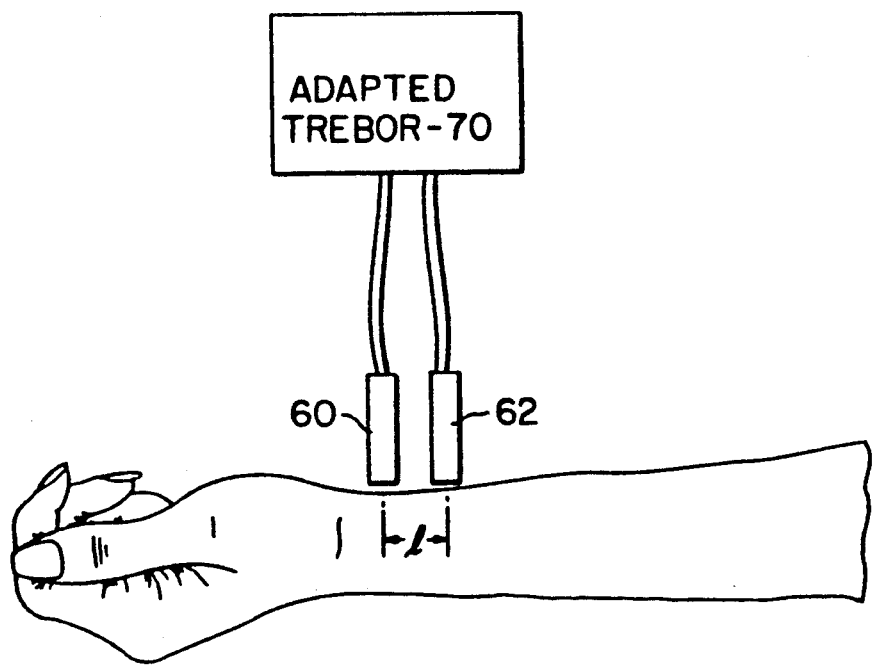
FIG. 4 illustrates one embodiment for practicing the inventive method.

An alternate procedure for practicing the inventive method is accomplished by the use of fiber optic light probes as seen in FIG. 4. These probes are connected with a near-IR analysis instrument such as the commercially available TREBOR-70 scanning spectrophotometer which has been adapted to process a signal for glucose analysis. A probe 60 is placed over the prominent vein and transmits near-IR energy of the desired wavelength(s). The near-IR energy interacts with the blood constituents and is collected by a second probe 62 placed over the vein a short distance l from first probe 60. A detector associated with the analytical instrument provides an electrical signal which is processed, as described above, to reveal quantitative information concerning blood glucose.

We have found that accurate quantitative analysis of blood glucose levels can be made at a variety of wavelengths with both interactance and transmittance technologies. In presently preferred embodiments illustrated in FIGS. 2A and 2B, near-IR light energy is transmitted through the finger of the test subject and then detected by an optical detector. As in the above described embodiments, a combination of measurement wavelengths is selected which emphasizes the glucose absorption and removes the effect of interfering absorption, for example, due to water, fat and protein.

Figure 2A:
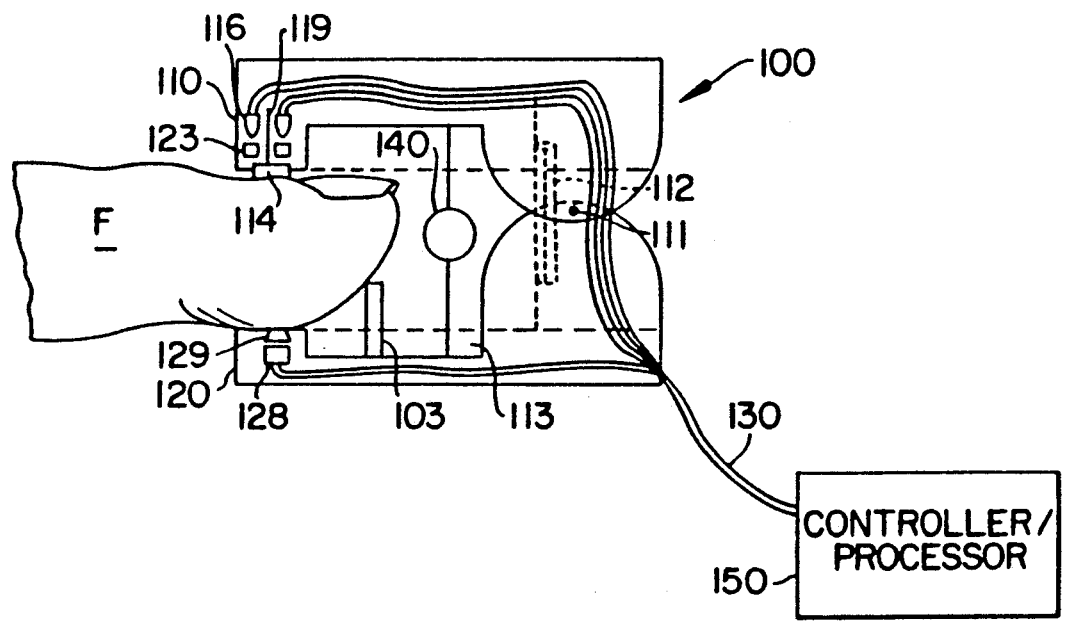
FIGS. 2A and 2B are partially schematic elevational views of alternate embodiments of near-infrared quantitative analysis instruments.

In the embodiment shown in FIG. 2A, a near-IR probe 100 is adapted to be placed over the finger F of a test subject and in this particular embodiment includes a point source means of near-IR light energy comprised of at least two IREDs 116 disposed within an upper flange 110. Each IRED is paired with a narrow bandpass optical filter 123 and is optically isolated via opaque light baffle 119. The inwardly-facing surface of flange 110 is provided with an optional optically clear window 114 for placement against the subject's finger.

Upper flange 110 is hinged about shaft 111 to lower flange 120, and a spring 112 serves to maintain the flanges in a closed position. An optical detector 128 is disposed in lower flange 120 opposite the near-IR source 116. The detector is disposed behind an optional window 129 which can be constructed of a material which is either optically clear or which excludes interfering light yet permits the desired near-IR light to pass. A finger stop 103 helps place and maintain the subject's finger in its proper position within the probe 100. Each of the flanges is provided with light-shielding barriers 113 (shown in phantom in FIG. 2A) to block ambient light from entering the probe.

In this embodiment the IREDs are pulsed, i.e. energized in sequence, so that the detector 128 receives light transmitted from only one of the IREDs at any one time. This pulsed IRED technology is described in U.S. Pat. No. 4,286,327 which is incorporated herein by reference. In other similar embodiments a group of IREDs (and optional narrow bandpass filters) with substantially identical center wavelength output can be pulsed.

Probe 100 is an electrical connection with a processor unit which is schematically illustrated in FIG. 2A. The processor unit houses a power source, signal amplifying, data processing and display circuitry as described in connection with the embodiment of FIG. 1 and standard in near-IR analysis instrumentation.

Figure 2B:
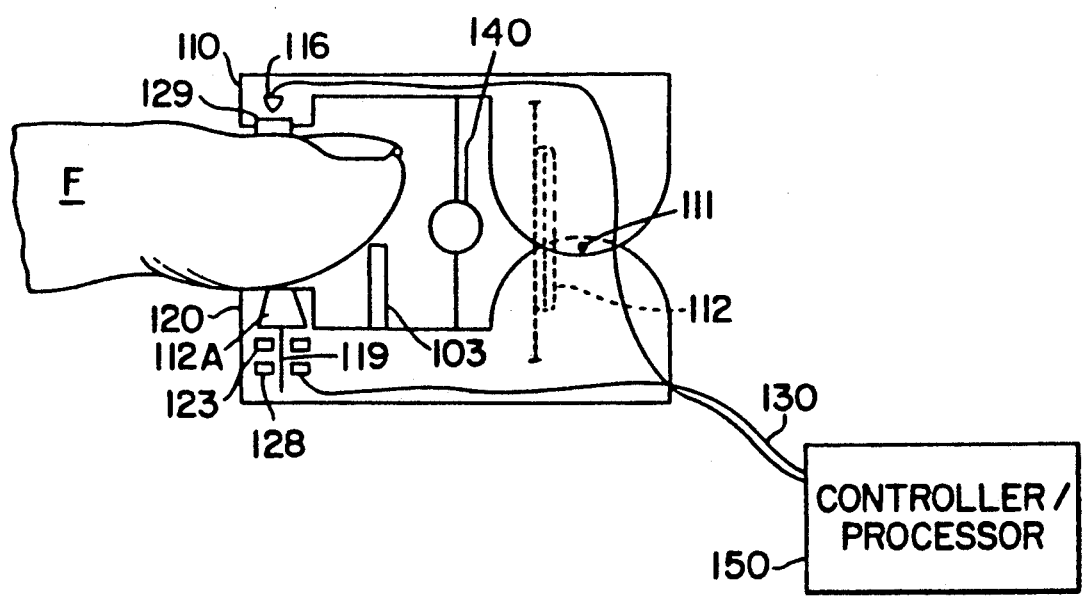

An alternate embodiment is seen in FIG. 2B. Here, probe 110 includes a single constant output IREDs 116 installed behind an optional window 129. Light transmitted through the finger is gathered by optical funnel 112A, which is constructed of a transparent or translucent material, and detected by multiple detectors 128. The detectors are optically isolated from one another by opaque light baffle 119. Each detector is paired with a narrow bandpass optical filter 123 and thus is set up to detect only light within the narrow wavelength range of its filter.

Near-IR point source means 116 can consist of one or more IREDs of known bandwidth and center frequency output or, as described above, can include a narrow bandpass optical filter within the light path to provide for the detection of only those wavelengths which are of interest. Multiple wavelengths can be utilized in transmission analysis and can be generated via multiple IREDs provided they are consecutively illuminated. Another approach is to use a single IRED with multiple bandpass filters which are mechanically moved through the light path as seen in FIG. 5. A third approach uses a single or group of IREDs capable of emitting a plurality of desired wavelengths with the use of multiple optical filters, each filter being associated with a respective detector. Single IREDs which emit two, three or four narrow bandwidths are commercially available.

In use, the finger of the test subject is inserted between the flanges 110 of the probe 100. Near-IR light energy is emitted by the point source means, is transmitted through the finger and is detected by optical detector 128. The electrical signals produced by the detectors are transmitted via line 130 to a controller/processor unit 150 where the signal is amplified and data processed using a suitable algorithm as described below. Blood glucose level is displayed on a readout device which preferably includes a digital display.

Accurate measurements of the concentration of blood glucose can be made using near-IR quantitative analysis algorithms which have only a single variable term, such as the following:

Approximated First Derivative Algorithm $$C = K_0 + K_1 [\log 1/I_G - \log 1/I_H]$$

Approximated Second Derivative Algorithm $$C = K_0 + K_1 [\log 1/I_A - 2 \cdot \log 1/I_B + \log 1/I_C]$$

Normalized First Derivative Algorithm $$C = K_0 + K_1 \frac{[\log 1/I_G - \log 1/I_H]}{[\log 1/I_I - \log 1/I_J]}$$

Normalized Second Derivative Algorithm $$C = K_0 + K_1 \frac{[\log 1/I_A - 2 \cdot \log 1/I_B + \log 1/I_C]}{[\log 1/I_D - 2 \cdot \log 1/I_E + \log 1/I_F]}$$

where C denotes concentration of glucose present in the blood, $K_0$ is the intercept constant, $K_1$ is the line slope of the variable term, and the log 1/I terms each represent an Optical Density (O.D.) value at a particular wavelength. In FIG. 6, an example of an overall absorbance curve for a test subject is shown, wherein log 1/I (O.D.) values for the above algorithms are plotted. In FIG. 6, optical energy is absorbed at wavelength B proportional to the constituent being measured, and optical energy is absorbed at wavelength E proportional to the total substance being measured. Points 150 and 152 are first derivative midpoints. The distance between, for example, wavelength G and wavelength H is referred to herein as the "gap" between two wavelengths. It has been found that a plurality of wavelength pairs, all centered on the same wavelength, can be used in the above algorithms. These algorithms are easily programmed into suitable microprocessor circuitry by those skilled in the art. The use of these single variable term equations is highly desirable because it allows simplified instrument calibration, thereby allowing the production of low cost instruments.

The intercept constant $K_0$ and the slope constant $K_1$ are determined by individually calibrating each unit.

Another class of usable near-IR standard algorithms involves the use of multiple regression terms. Such terms can be individual log 1/I terms or can be a multiple number of first or second derivative terms with or without a normalizing denominator. Such multiple terms may provide additional accuracy, but introduce higher calibration expense which results in a more expensive instrument.

Data on a plurality of physical parameters of the test subject can also be utilized in conjunction with multiple wavelength measurement of near-infrared interactance, as in prior U.S. Pat. No. 4,633,087, to improve the accuracy of the present blood glucose measurements.

Selection of combinations of wavelengths which emphasize glucose absorption and removes possible interfering absorptions can be performed by computer search studies. In general, a suitable combination of wavelengths will include at least one wavelength which is sensitive to blood glucose, and at least one wavelength which is insensitive to blood glucose (reference wavelength). The following examples show results of wavelength search studies, which are provided herein for illustrative purposes only, and are not to be construed in a limiting sense.

EXAMPLE I

Figure 7:
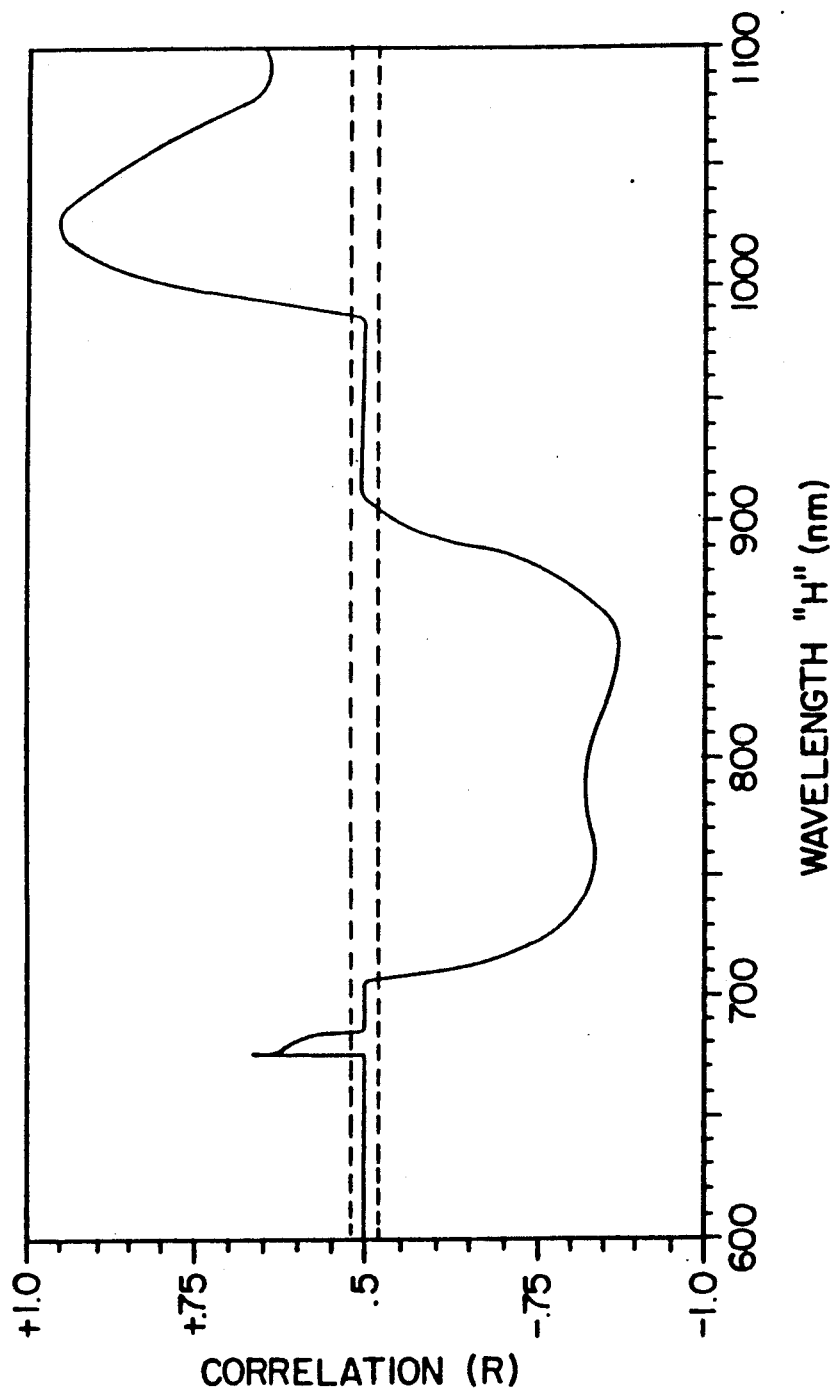
FIG. 7 illustrates a wavelength search study via a plot of correlation coefficient versus wavelength.

FIG. 7 presents correlation coefficient versus wavelength data from a search study utilizing an approximated first derivative algorithm as defined above, and illustrates that the use of the wavelength pair of 980 ± (plus and minus) 35 nm provides a high correlation between blood glucose and absorption of near-IR energy at those two wavelengths. FIG. 7 utilizes the above approximated first derivative algorithm, wherein G and H are as shown in FIG. 6, and equal to 945 nm and 1015 nm respectively. Thus, in this example, the "gap" is 70 nm (1015 nm−945 nm). The number of samples tested was 30 in this case. The value of $K_0$ in the approximated first derivative algorithm is 196.9 and for K is 4,802.6. In this case, the standard deviation was 13.54, with a correlation of +0.948. Reference numeral 154 of FIG. 7 indicates a range of candidates for wavelength H with a "gap" equal to 70 nm and a "smoothing" factor of 41. "Smoothing" is the modification of data derived from a scanning spectrophotometer in order to simulate the results which would be obtained at the half power bandwidth of optical filters. "Smoothing" involves taking log 1/I data at an equal number of wavelengths above and below each wavelength of interest and averaging the results. Thus, with a "smoothing" value of 41, data is taken at 20 wavelengths above and 20 wavelengths below the bandwidth of interest, in addition to each wavelength of interest. An example of one embodiment of the invention uses IREDs which provide near-IR energy at two frequencies which are, respectively, equidistant above and below approximately 980 nm, i.e., they can be represented by the formula 980±x nm. The value of x is not unduly critical so long as the two frequencies are centered on approximately 980 nm. A suitable value for x can be, for example, a number from 10 to 40.

EXAMPLE II

FIG. 8A shows that a suitable wavelength for a numerator in the above normalized first derivative algorithm is approximately 1013 nm (i.e., 980 nm+35 nm) wherein $K_0=296.8$, $K_1=-175.6$, "gap" G-H: 70 nm, wavelength J: 915 nm, "gap" I-J:20 nm, standard deviation=12.21 and correlation=−0.958 (30 samples).

EXAMPLE III

Figure 8:
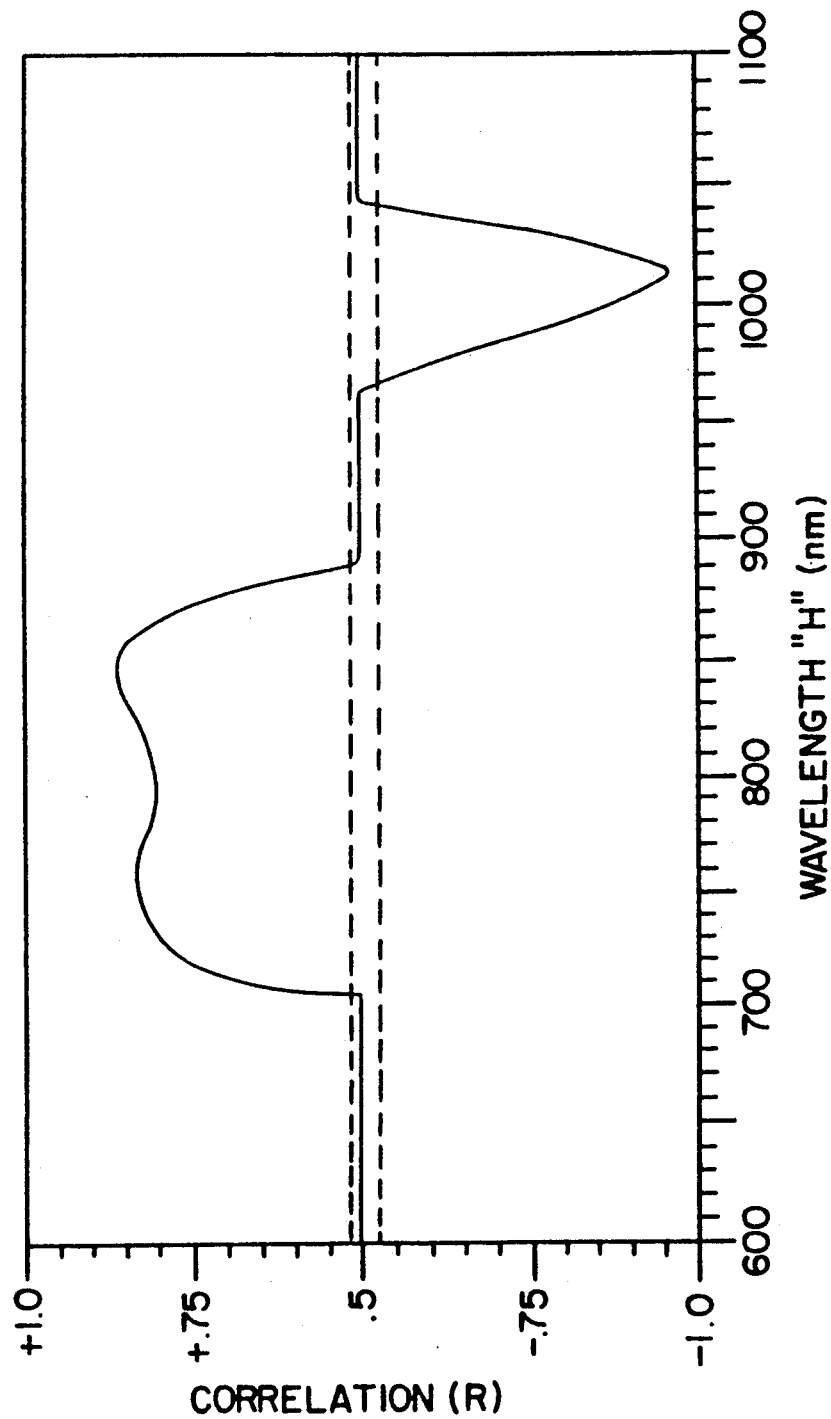
FIGS. 8 and 9 illustrate plots of correlation coefficient versus wavelength for first derivative equations.
Figure 9:
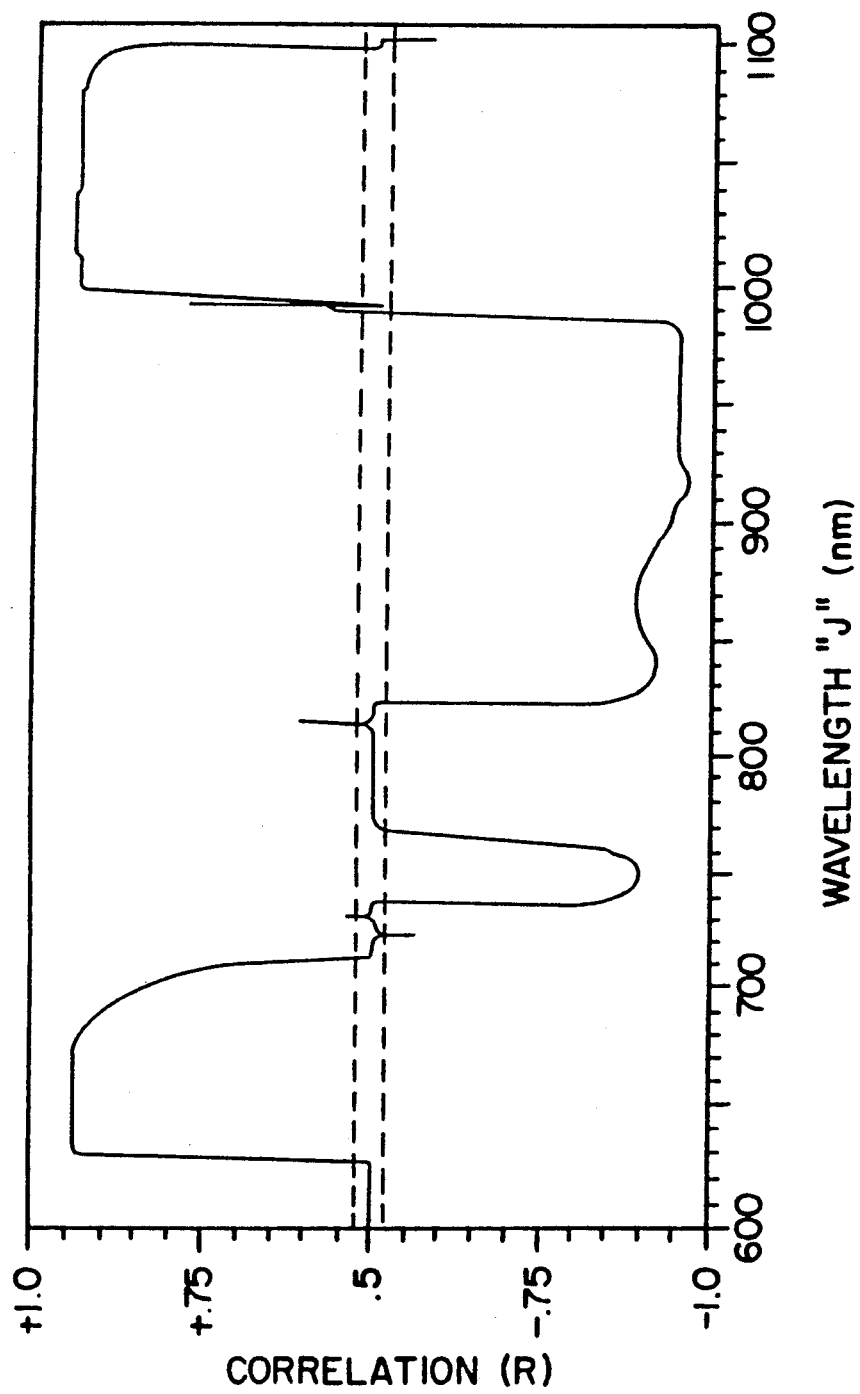

FIG. 9 shows that there are many wavelength regions that can provide midpoint wavelengths for use in the denominator of the above normalized first derivative algorithm when the numerator utilizes 980±35 nm wavelengths, wherein $K_0$, $K_1$, "gap" G-H, gap I-J, standard deviation, correlation and sample size are the same as in Example II and FIG. 8, and wherein wavelength H is 1013 nm. Examples of such wavelength regions are seen to be from 610 to 660 nm, from 910 to 980 nm and from 990 to 1080 nm.

EXAMPLE IV AND V

Figure 10:
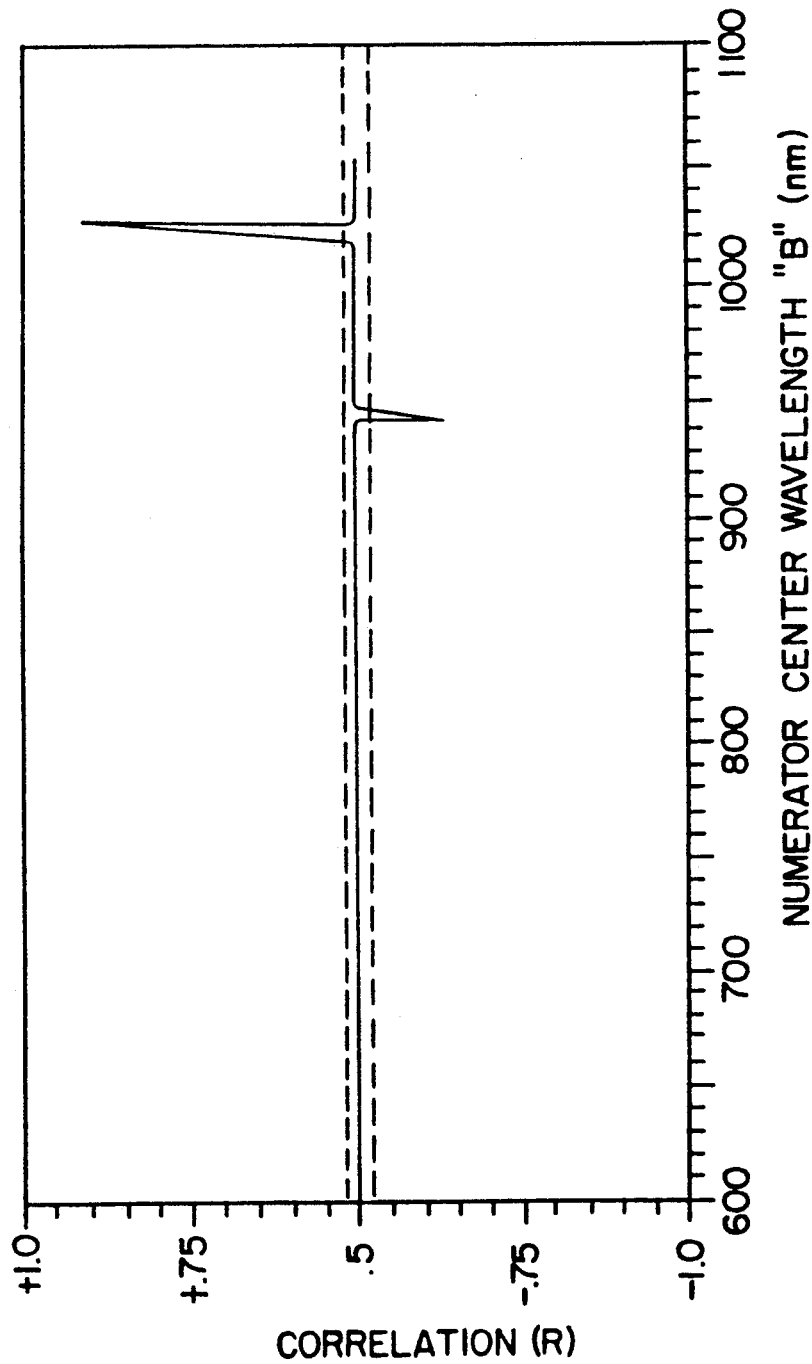
FIGS. 10 and 11 illustrate plots of correlation coefficient versus wavelength for second derivative equations.
Figure 11:
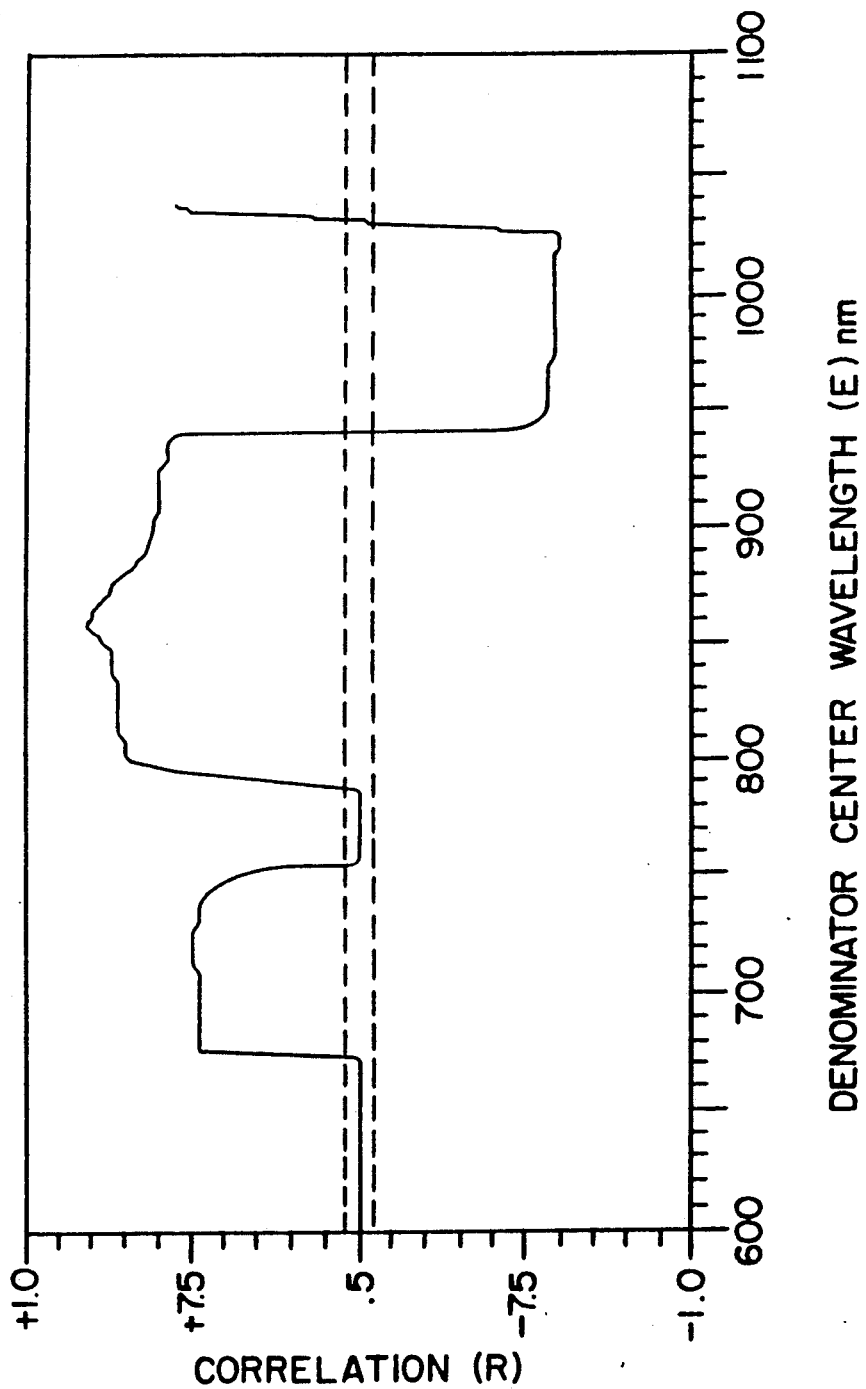

FIGS. 10 and 11 illustrate optimum center wavelengths for use in the normalized second derivative algorithm described above. FIG. 10 is a plot of correlation coefficient versus wavelength which shows that a suitable numerator center frequency is approximately 1020 nm, wherein in the above normalized second derivative algorithm, $K_0=205,856$, $K_1=356.457$, "gap" A-B and B-C=to 53 nm, wavelength E: 850 nm, "gap" D-E and E-F=to 68 nm and standard deviation=20.44 (47 samples). FIG. 11 shows that a denominator center frequency of about 850 nm is suitable, wherein $K_0$, $K_1$, "gap" A-B and B-C, "gap" D-E and E-F, standard deviation, and sample size are as in FIG. 10, and wherein wavelength B is 1020 nm.

The accuracy of this preferred near-IR transmission embodiments shown in FIGS. 2A and 2B can be further improved by altering the algorithm to include finger thickness as a parameter. According to Lambert's law, energy absorption is approximately proportional to the square of the thickness of the object. The thickness of the test subject's finger can be quantified by installing a potentiometer 140 between the flanges of the probe 100 as seen in FIGS. 2A and 2B. The output of the potentiometer, which is in electrical connection with the data processing circuitry, is indicative of finger thickness. A non-linear potentiometer can approximate the $T^2$ value via its output alone so that a separate squaring calculation step is not necessarily required.

Figure 12:
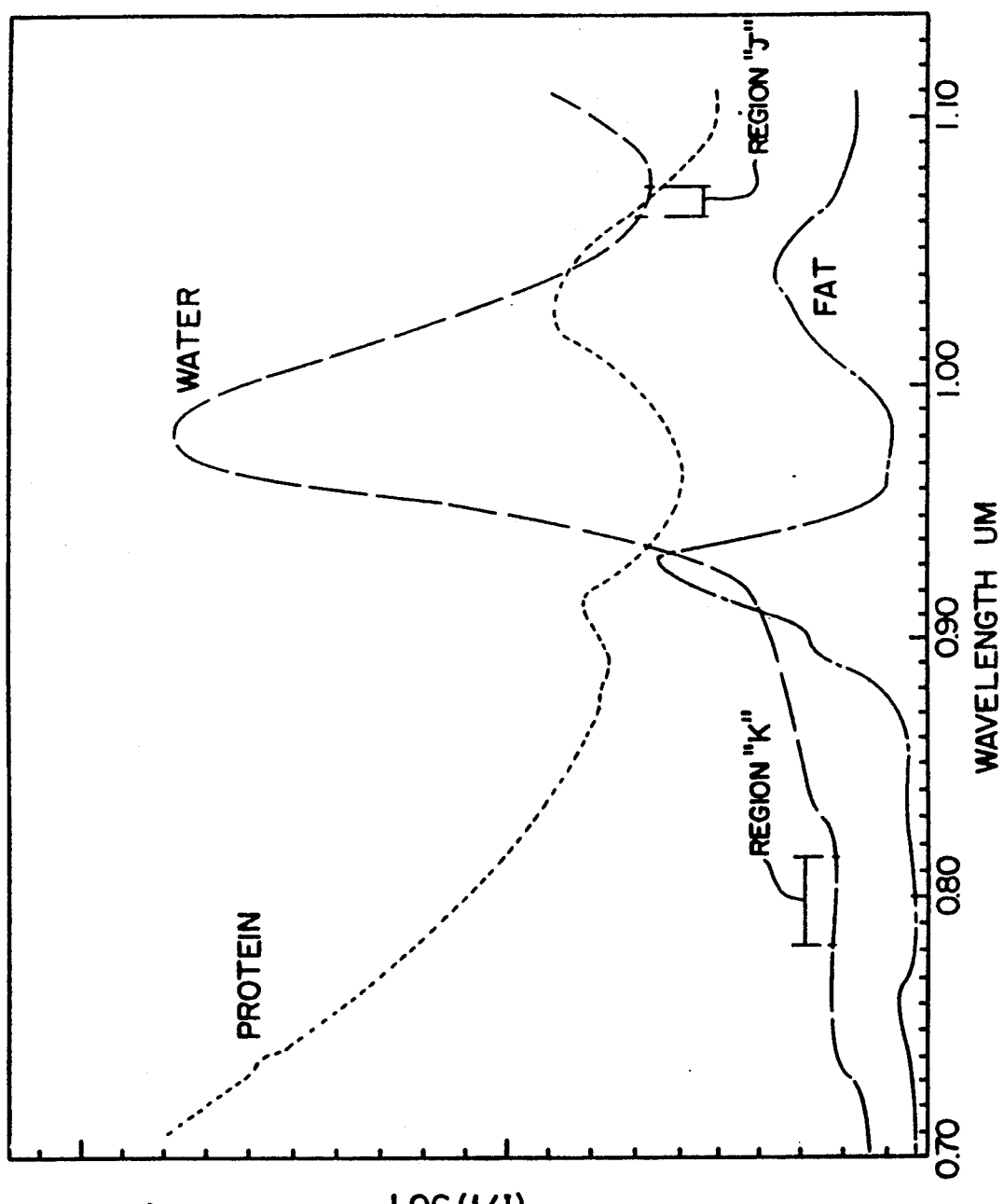
FIG. 12 is a plot of log (1/I) versus wavelength which illustrates near-infrared energy absorption by water.

Selection of suitable combinations of measurement wavelengths can take into account the identification and removal of possible interfering absorptions, such as due to water. FIG. 12 illustrates that water is one of the strongest absorbers of near-IR energy. The effect of this inherent strong absorption is magnified by the very high water content in the human body (i.e., approximately 60% for the average person). Thus, measurements in the near-infrared must be performed with care to avoid being distorted due to slight changes in body water caused by either dehydration (e.g., perspiration) or due to excessive intake of fluids.

This care is particularly critical when trying to measure blood glucose. This is because of the extremely low concentration of glucose level in the blood (average of approximately 100 milligrams per deciliter).

Figure 13:
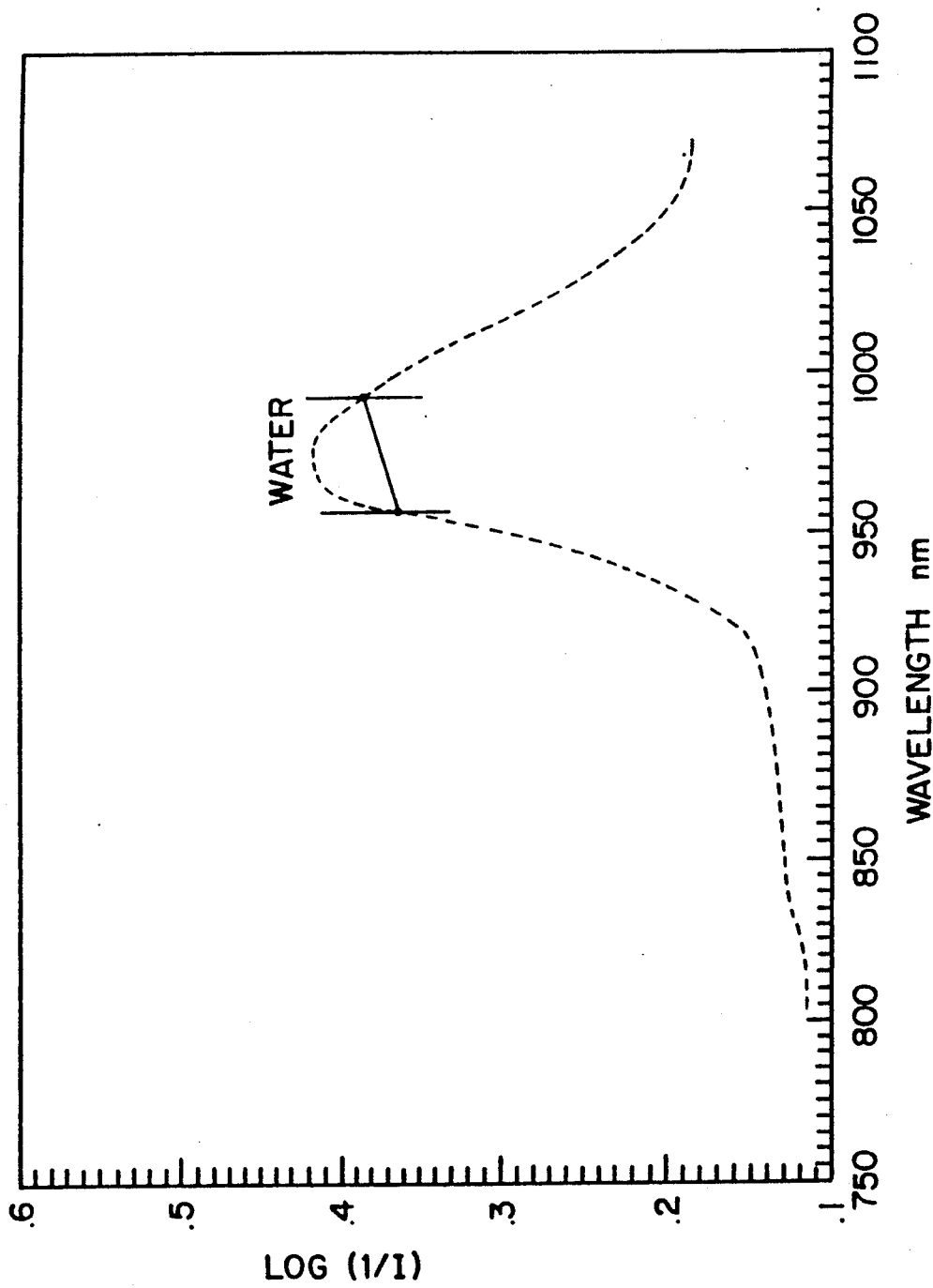
FIG. 13 is a plot of log (1/I) versus wavelength illustrating two measurement wavelengths which stradle a water band.

The wavelength search studies discussed above illustrate that where the mid-wavelength between the two measurement wavelengths would be approximately at the center of a water "dead band" (i.e., minimal interference due to water), good measurement has been provided (See FIG. 7). The reasons for this is that these two measurement wavelengths straddle the water "dead band", and thereby, minimize errors due to the change in water content. FIG. 13 illustrates that the two measurement wavelengths which straddle the water band correspond to the wavelength pair in FIG. 7 which provides a high correlation between blood glucose and absorption of near-IR energy.

Figure 14:
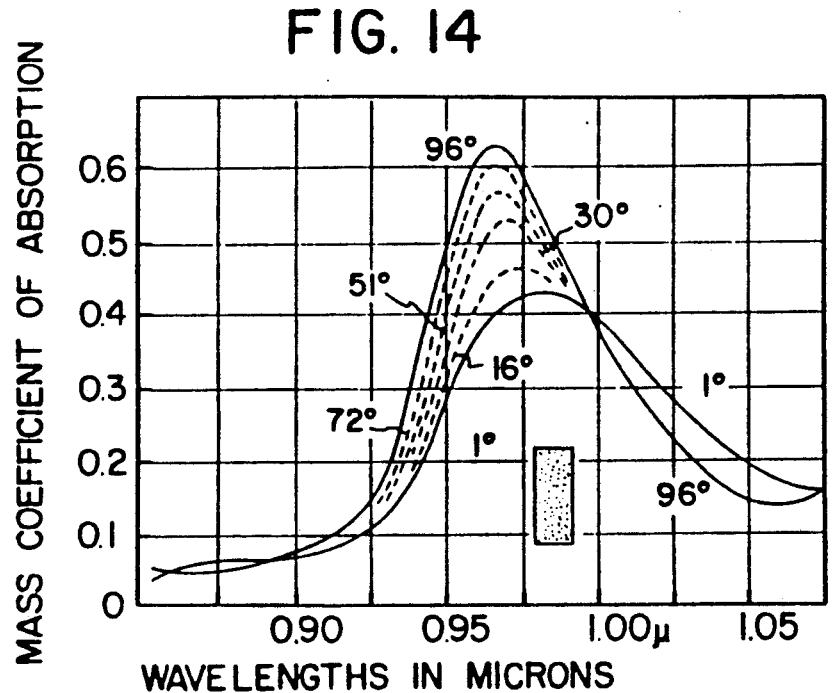
FIG. 14 illustrates that energy absorption by water varies with temperature.

However, FIG. 14 illustrates the well known phenomenon that the water absorption curve varies with change in temperature. Since temperature at different extremities on the body can vary for a variety of reasons such as due to illness or from ingestion of cold or hot fluids/foods, the potential for error in glucose measurement made where the wavelength pair straddles the water band may become excessive.

To overcome this potential temperature limitation, two regions of the spectrum have been discovered that appear to be well suited for measurement of blood glucose. These are indicated as Region "J" and Region "K" in FIG. 12 for the standard near-IR absorption curve for water. In Region "J", the water absorption curve reaches a minimum near 1070 nm. In this region, changes in water concentration would have the least effect of any place in the longer wavelength spectrum.

Figure 15:
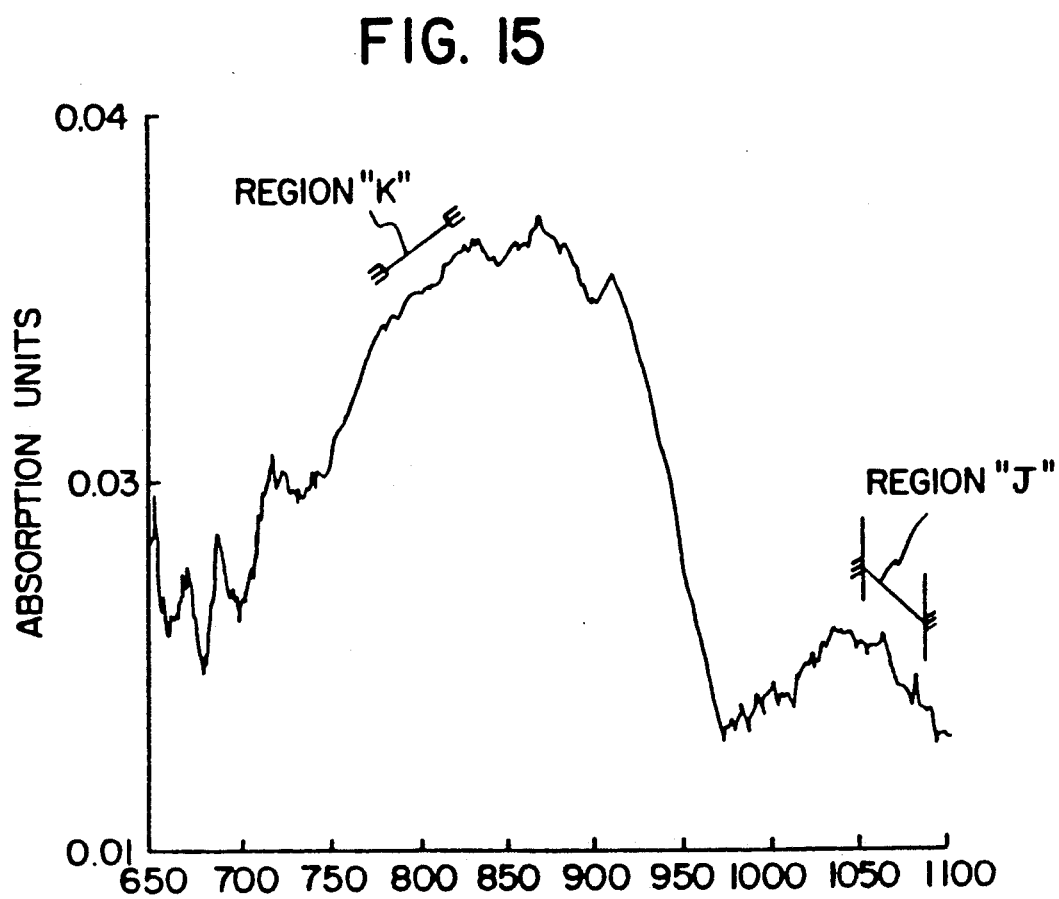
FIG. 15 illustrates a difference spectra of glucose absorption of near-infrared energy in the body.

FIG. 15 illustrates the effective spectra of glucose in the human body. This spectra was developed by subtracting two spectra obtained by transmitting optical energy at 1 nm intervals between 600 to 1100 nanometers through the distal portion of the index finger. The two scans were made approximately one hour apart during which time the subject drank a concentrated solution of dextrose, thereby raising the blood glucose level. Thus, this difference spectra in FIG. 15 is primarily due to glucose.

As shown in this figure, there is a broad absorption due to glucose that occurs between 850 and 900 nm as well as another one that occurs at approximately 1050 nm. Although other absorptions are occurring, they are not as well defined.

The glucose absorption that occurs at approximately 1050 nm causes a negative slope between approximately 1070 to 1100 nm (See FIG. 12, Region "J"). This negative slope is measured by using two log 1/I measurements for example, one at approximately 1070 nm and the other one at approximately 1090, and coincides favorably with the nadir point on water absorption curve (i.e., Region "J" FIG. 12). Thus, a change in body water level would have minimal affect on the glucose reading in this area.

As stated above, one of the parameters affecting near-infrared accuracy is change in temperature of the subject being measured. Although there appears to be little actual relationship between finger temperature and glucose level, it has been discovered that by adding a temperature term to the regression equation, a significant improvement in correlation coefficient occurs. The temperature term can be added to any of the near-IR quantitative analysis algorithms identified as providing accurate measurements of concentration of blood glucose, such as the following:

$$C = K_0 + K_1 [\log 1/I_A - \log 1/I_B] + K_2 T_1$$

where C denotes concentration of glucose present in the blood, $K_0$ is the intercept constant, $K_1$ is the line slope of the variable term, $K_2$ is a calibration constant, the log 1/I terms each represent an Optical Density (O.D.) value at a particular wavelength and $T_1$ represents the local surface temperature of the body where the optical reading is being made. The temperature term $T_1$ can also be added to the algorithms for three, four or six wavelengths described above.

Figure 16:
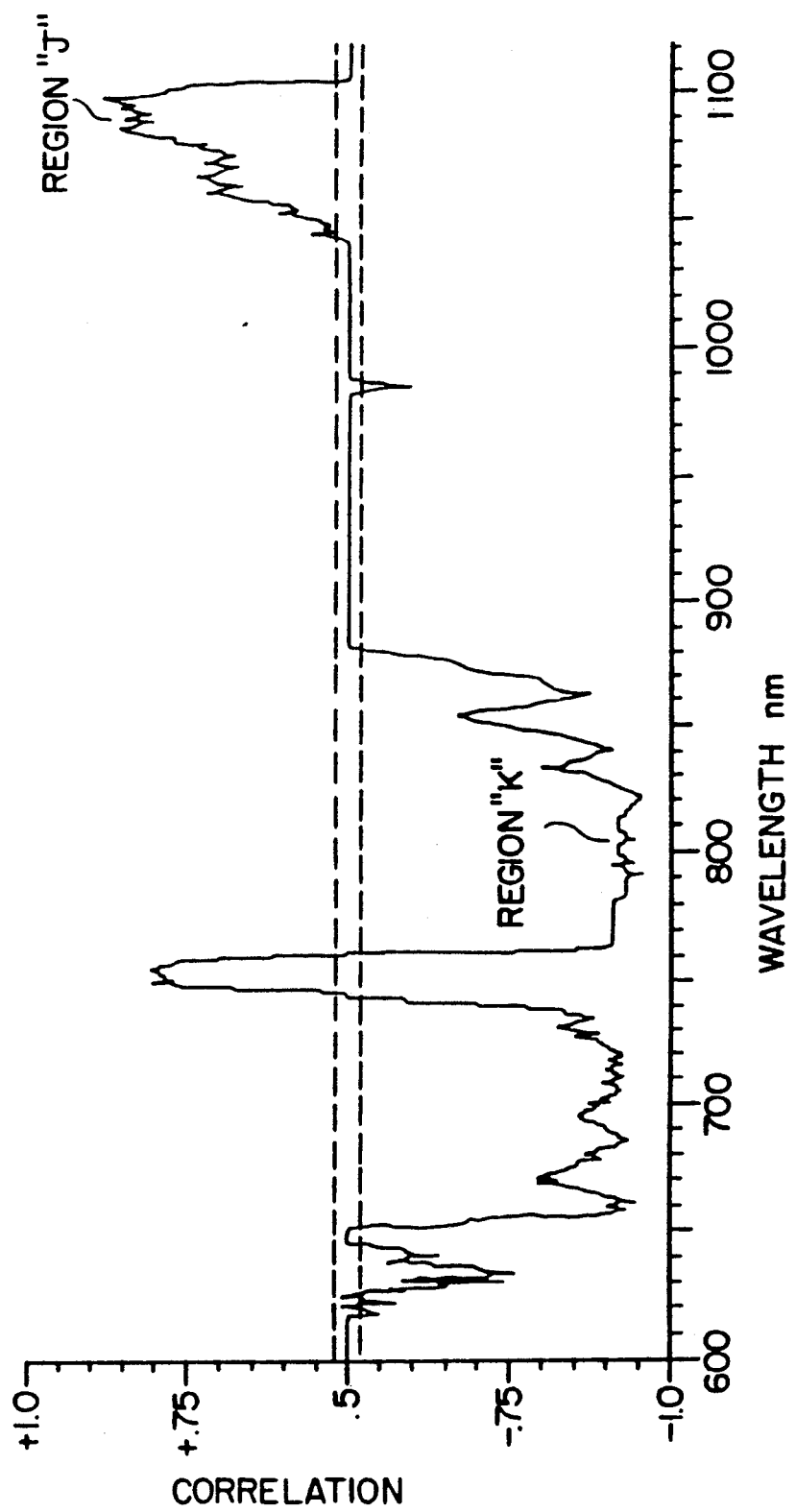
FIG. 16 is a plot of correlation versus wavelength illustrating the effect of a temperature term in the linear regression equation.

FIG. 16 illustrates the improved correlation coefficients obtained in the Region "J" band using the temperature term $T_1$ in the linear regression equation. Although the correlation in Region "J", approximately 1080 nm, is not the highest of any wavelength, it is of a level useable for a commercial instrument, particularly if consideration is given to potential errors introduced due to change in body water level.

In addition to the Region "J" band, the Region "K" band provides a unique measurement candidate for glucose. FIG. 12 shows that the water curve has no significant slope from 780 nm to 810 nm (Region "K"). This water "dead band" provides a good wavelength region to measure glucose, as shown by the relatively steep slope of glucose in this region (See FIG. 15).

Figure 17:
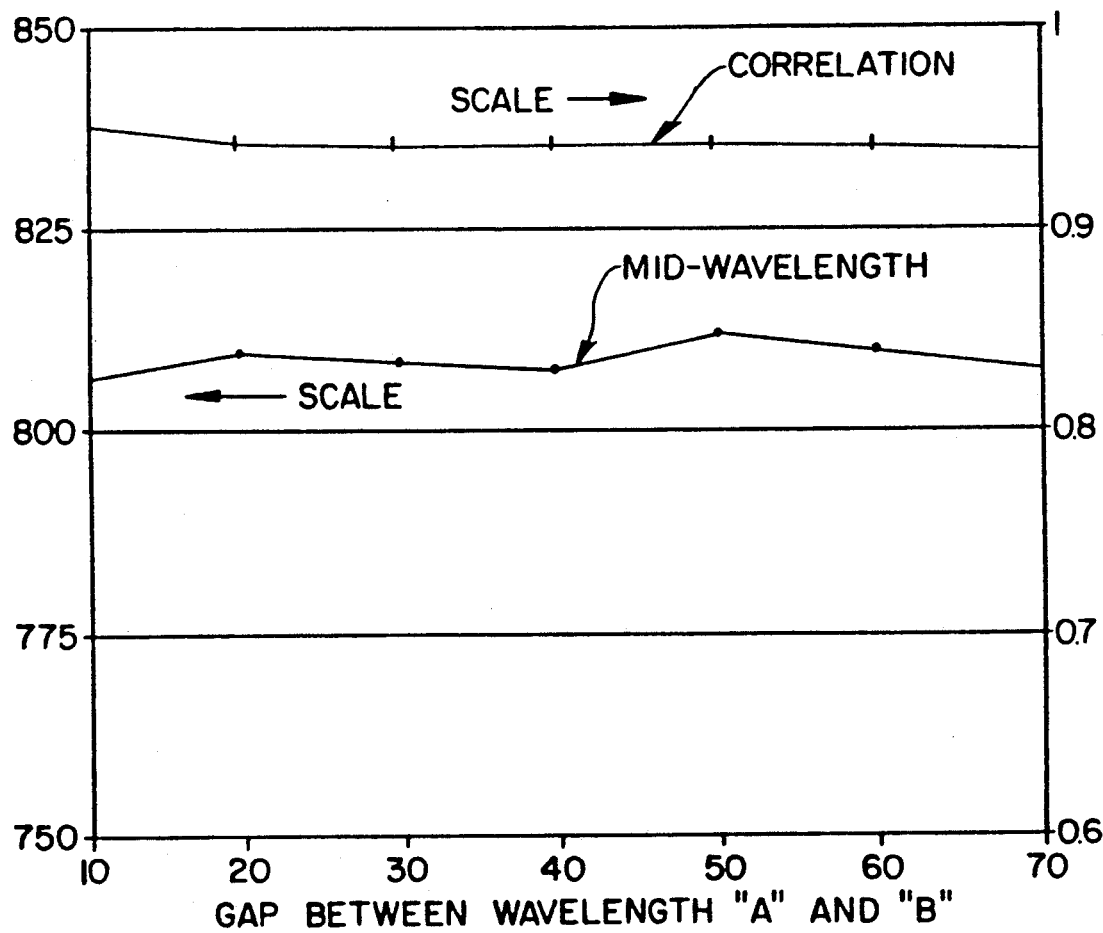
FIG. 17 is a plot of mid-wavelength and correlation versus gap between wavelength "A" and "B"

FIG. 17 further demonstrates the uniqueness of this Region "K". It shows that the "mid-point" wavelength (i.e., the wavelength halfway between wavelength "A" and wavelength "B") remains essentially constant independent of gap size. This is due to the "dead band" (i.e., no interference due to water). The importance of this Region "K" is further demonstrated by the fact that correlation coefficient remains high (between 0.94 and 0.95) independent of gap size.

Another parameter affecting near-infrared analysis accuracy is ambient temperature change within the measurement instrument. It is known that the output of silicon optical detectors (the detector of choice in the spectrum regions of 600 to 1100 nm) is extremely sensitive to temperature changes. Thus, varying the "room temperature" could have negative effect on measurement reliability. By adding a third term to the regression equation, i.e., an ambient temperature term, a significant improvement in the correlation coefficient occurs. The ambient temperature term can be added to any of the near-IR quantitative analysis algorithms identified above, such as the following:

$$C = K_0 + K_1 [\log 1/I_A - 2 \cdot \log 1/I_B] + K_2 T_S + K_3 T_A$$

wherein each term described above is the same, $K_3$ is a calibration constant and $T_A$ represents the ambient temperature within the measurement instrument. The ambient temperature term can also be added to the algorithms for three, four or six wavelengths as described above.

In a preferred embodiment, a thermistor is used to measure the instrument's ambient temperature. Although alternative means could be used, a thermistor is the most practical solution for a battery powered instrument.

Accurate measurements of the concentration of blood glucose can be made using any suitable algorithm described above utilizing either two, four or six wavelengths. The two wavelength model provides the lowest cost instrument since only two optical measurements need be made. The applicability of the two wavelength model has been verified by repeatedly testing a group of diverse people, such as those of different racial origins, sex, body fat and those without a history of diabetes. These tests demonstrated high correlation coefficients obtained (e.g., typical correlation coefficients exceed 0.93). Further, tests indicated that wavelengths "A" and "B" which provided the highest correlation were substantially different for each person.

This "wavelength uniqueness" for each person directly results from the individual's organic body composition. The human body is primarily composed of water (55% to 70%), fat (5% to 40%), and protein (5% to 15%). These three constituents add up to more than 95% of the total body composition. Since water, fat and protein all have strong near-IR absorption bands, the measurement of glucose (concentration of less than 0.1% of the body) must be made at wavelengths that have minimum interference by these major near-IR absorptions.

Since each individual has a different relative body composition, the minimum interference points where glucose can be measured differs greatly between individuals. In some instances, this change in wavelength can be as much as 50 nm. Tables I and II reproduced below illustrate this difference. The tables show the correlation coefficient versus measurement wavelength for three different individuals. A constant difference between A and B of 10 nm was retained for the measurements. As shown in Table I, Subject A's optimum "B value" was at 820 nm, where Subject B's optimum "B value" was at 790 nm, and Subject C's optimum "B value" was at 840 nm.

TABLE I

Figure 18A:
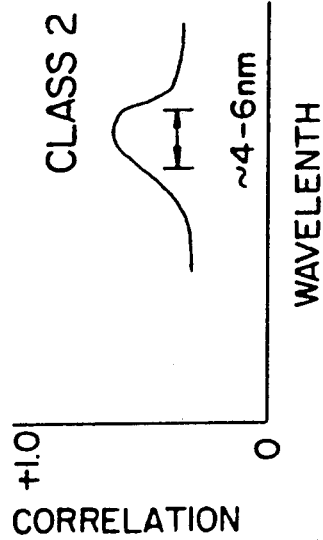
FIGS. 18A–D illustrate classes of peaks which correspond to the shape of a correlation versus wavelength curve.

FIG. 18A
Two Wavelength Model
For Halfpower Bandwidth = 15 nm

| Person | R Correlation | "B" nm | GAP (A-B) |
|--------|---------------|--------|-----------|
| A | .92 | 790 | 10 |
| A | .95 | 820 | 10 |
| A | .90 | 840 | 10 |
| B | .93 | 790 | 10 |
| B | .88 | 820 | 10 |
| B | Low | 840 | 10 |
| C | Low | 720 | 10 |
| C | .88 | 820 | 10 |
| C | .97 | 840 | 10 |

TABLE II

Figure 18B:
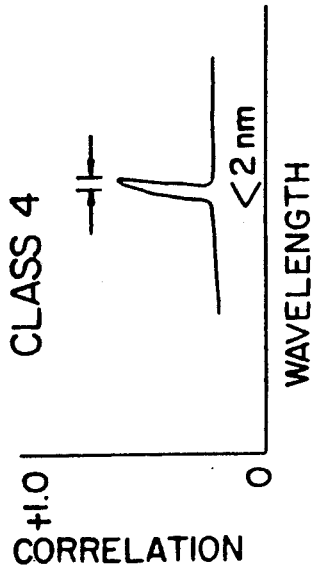

FIG. 18B
Two Wavelength Model
For Halfpower Bandwidth = 60 nm

| R Correlation | "B" nm | GAP (A-B) |
|---------------|--------|-----------|
| .93 | 790 | 10 |
| .93 | 820 | 10 |
| .91 | 840 | 10 |
| .92 | 790 | 10 |
| .89 | 820 | 10 |
| .84 | 840 | 10 |
| Low | 790 | 10 |
| .84 | 820 | 10 |
| .86 | 840 | 10 |

The Table I measurements were made using a near-IR source having an optical half power band width of approximately 15 nm. This half power band width is commonly used for near-infrared measurements and it can be provided by placing a narrow bandpass optical filter in front of an infrared emitting diode.

Table II illustrates the same data as Table I except for the use of a very wide half-power band width. The half-power band width shown in Table II is equivalent to that provided by an infrared emitting diode without any optical filter (approximately 60 nm). As shown in Table II, there is an accuracy penalty incurred by using these wide band widths. However, with this approach the production of a lower cost instrument becomes possible because the optical filters can be omitted. Further, it is recognized that in some cases, this penalty in accuracy would be acceptable.

In the algorithms provided above, the two temperature terms $T_S$ and $T_A$ are not optical variables in that they can be measured by independent thermistors. For this reason, the constants $K_2$ and $K_3$ may not vary between instruments.

According to one embodiment of the present invention, a non-invasive blood glucose instrument is constructed which provides an accurate blood glucose level measurement correcting for inaccuracies resulting from each person's "wavelength uniqueness." In the lightweight, hand-held analysis instrument 50 illustrated in FIG. 19, included is a means for providing at least one point source of near infrared energy. The near-infrared point source means is positioned so that near-infrared energy being emitted from the point source means will be focused by a lens 51 through window 53 and onto the skin of the test subject. The near-infrared energy emerging from the test subject will travel through window 54 and be detected by detector 55. Detector 55 is electrically connected to controller/processor 56 which calculates the test subject's blood glucose level. In one embodiment of the present invention, also illustrated in FIG. 19, the blood glucose measurement instrument 50 is constructed having a first section 60 and a second section 61 pivotally connected together by hinge 58. Spring 62 is connected to first section 60 and second section 61 and facilitates securing the instrument against the test subject's skin thereby substantially shielding interfering ambient light from detector 55.

In a preferred embodiment, the near infrared point source means may comprise six IREDs 52 (FIG. 19 shows only two). The center wavelength of each IRED can be separated by a constant wavelength, for example, an IRED with a center wavelength at 790 nm, the next at 800 nm, etc. (i.e., center wavelengths from 790 nm to 850 nm). The use of IREDs as a light source allows a simple, low-cost instrument to be developed. Also, this instrument could contain just one IRED and utilize the configurations in FIGS. 5A and 5B for interposing optical filters 23' and 23" respectively in the light path.

In the embodiment of the present invention utilizing a plurality of IREDs, each IRED is sequentially pulsed. As illustrated in FIG. 19, microprocessor 56 is used to sequentially pulse each IRED. Microprocessor 56 can also be used to custom calibrate the instrument to a specific individual. This is accomplished by measuring the person at a time of low glucose level such as after an overnight fast. The person then increases his glucose concentration by, for example, drinking a dextrose solution, and is again measured. The microprocessor can be used to determine which two IREDs provide the maximum difference, and then use those IREDs in subsequent glucose measurements for that individual.

However, if better accuracy is required, optical filters could be used with the IREDs. In such a case, a "filter tray" containing a plurality interchangeable optical filters could be made available to, for example, a medical professional. The medical professional would have a master instrument that can be used in conjunction with glucose tolerance test. This master instrument would be used to define the optimum wavelength for a specific individual. Moreover, it would define the instrument's calibration constants for that individual as well.

The medical professional could then place the correct optical filters that correspond to what was found on the master instrument into a small portable home instrument. These optical filters would be installed using the "filter tray" discussed above, thereby, customizing a home instrument for that specific individual. Likewise, the calibration constants will also be entered into the instrument by the medical professional.

In another embodiment of the present invention, the four wavelength model enables accurate glucose measurement testing and has as a major advantage that the wavelengths would not have to be varied for each individual tested. One set of wavelengths is applicable for all people.

Table III reproduced below presents a comprehensive listing of candidate wavelength combinations for this model. This data (as well as the six wavelength model candidates) was derived from actual tests on three separate individuals, two of which were diabetics. These tests included a minimum of 200 separate measurements on each person while their blood glucose varied considerably by undergoing glucose tolerance tests. Because of the diversity of these individuals, it is believed that the data shown is reasonably representative of the general population.

TABLE III

DELTA OD/DELTA OD; ALL REASONABLE CANDIDATES
(R > .8)
Criteria: Must be OK on 3 People; "$R_{min}$" is lowest correlation coefficient of the lowest person.

| NUM "B" | GAP (A-B) | Class | Region | DEN "E" | GAP (D-E) | $R_{MIN}$ |
|---|---|---|---|---|---|---|
| 705 | 10 | 4 | D | 650 | 30 | .91 |
| 711 | 20 | 4 | D | 650 | 10 | .87 |
| 1091 | 20 | 3 | A | 650 | 20 | .85 |
| 1087 | 20 | 4 | A | 660 | 10 | .84 |
| 1090 | 20 | 3 | A | 670 | 10 | .84 |
| 1088 | 20 | 4 | A | 680 | 10 | .84 |
| 1088 | 20 | 3 | A | 690 | 10 | .85 |
| 1092 | 30 | 3 | A | 700 | 10 | .90 |
| 1089 | 20 | 4 | A | 710 | 10 | .82 |
| 1092 | 20 | 4 | A | 730 | 10 | .86 |
| 1089 | 20 | 4 | A | 740 | 10 | .85 |
| 1090 | 20 | 3 | A | 750 | 10 | .85 |
| 627 | 10 | 3 | D | 820 | 10 | .90 |
| 676 | 10 | 4 | D | 820 | 10 | .85 |
| 940 | 10 | 1 | Other | 820 | 10 | .89 |
| 1093 | 20 | 3 | A | 820 | 10 | .86 |
| 637 | 20 | 4 | D | 830 | 10 | .82 |
| 828 | 20 | 3 | B | 830 | 10 | .85 |
| 942 | 20 | 1 | Other | 840 | 20 | .89 |
| 1091 | 20 | 3 | A | 830 | 10 | .86 |
| 630 | 20 | 4 | D | 840 | 10 | .83 |
| 960 | 20 | 1 | Other | 840 | 10 | .85 |
| 996 | 20 | 2 | Other | 840 | 10 | .90 |
| 1045 | 10 | 1 | Other | 840 | 10 | .82 |
| 1091 | 20 | 2 | A | 840 | 10 | .88 |
| 819 | 20 | 3 | B | 850 | 10 | .85 |
| 1088 | 20 | 4 | A | 850 | 10 | .84 |
| 627 | 20 | 3 | D | 860 | 10 | .85 |
| 1088 | 20 | 3 | A | 860 | 10 | .99 |
| 1089 | 20 | 3 | A | 870 | 10 | .85 |
| 1089 | 20 | 3 | A | 880 | 10 | .87 |
| 825 | 20 | 3 | B | 890 | 10 | .84 |
| 1089 | 20 | 3 | A | 890 | 10 | .85 |
| 825 | 20 | 3 | B | 900 | 10 | .85 |
| 1089 | 20 | 3 | A | 900 | 10 | .85 |
| 828 | 30 | 3 | B | 910 | 10 | .83 |
| 1088 | 20 | 2 | A | 910 | 10 | .86 |
| 837 | 30 | 2 | B | 920 | 10 | .84 |
| 1088 | 20 | 2 | A | 920 | 10 | .86 |
| 838 | 30 | 2 | B | 930 | 10 | .87 |
| 1088 | 20 | 3 | A | 930 | 10 | .85 |
| 820 | 10 | 2 | B | 940 | 10 | .87 |
| 832 | 20 | 1 | B | 940 | 10 | .87 |
| 837 | 30 | 2 | B | 950 | 10 | .87 |
| 838 | 30 | 2 | B | 960 | 10 | .84 |
| 838 | 30 | 2 | B | 970 | 10 | .87 |
| 1091 | 20 | 3 | A | 980 | 10 | .86 |

TABLE III-continued

DELTA OD/DELTA OD; ALL REASONABLE CANDIDATES
(R > .8)
Criteria: Must be OK on 3 People; "$R_{min}$" is lowest correlation coefficient of the lowest person.

| NUM "B" | GAP (A-B) | Class | Region | DEN "E" | GAP (D-E) | $R_{MIN}$ |
|---|---|---|---|---|---|---|
| 1091 | 20 | 2 | A | 990 | 10 | .86 |
| 1091 | 20 | 3 | B | 1000 | 10 | .86 |
| 819 | 10 | 3 | B | 1010 | 10 | .81 |
| 1088 | 20 | 2 | A | 1010 | 10 | .86 |
| 1088 | 20 | 2 | A | 1020 | 10 | .86 |
| 1088 | 20 | 2 | A | 1030 | 10 | .86 |
| 1088 | 20 | 2 | A | 1040 | 10 | .86 |
| 1088 | 20 | 2 | A | 1050 | 10 | .86 |
| 1088 | 20 | 2 | A | 1060 | 10 | .86 |
| 705 | 20 | 4 | C | 1070 | 10 | .84 |
| 1091 | 30 | 4 | A | 1070 | 10 | .87 |
| 698 | 10 | 2 | C | 1080 | 10 | .92 |
| 788 | 10 | 1 | B* | 1080 | 10 | .93 |
| 791 | 20 | 1 | B* | 1080 | 10 | .93 |
| 980 | 40 | 4 | Other | 1080 | 10 | .91 |
| 1091 | 10 | 3 | A | 1080 | 10 | .87 |
| 1088 | 20 | 3 | A | 1100 | 10 | .82 |

*Short Wavelength Side

Selecting the best wavelength candidates for this four wavelength model involves a tradeoff of competing considerations such as the degree of accuracy that is necessary (e.g., for general population screening tests, a lower accuracy may be acceptable compared to a high level of accuracy needed for measuring and controlling the insulin dosage of a diabetic) and typical instrument design parameters such as product cost (e.g., usability of low cost IRED's as the light source instead of the high power requirement of a filament type light bulb). In addition, the minimum risk of encountering an erroneous blood glucose reading is considered as well.

The data in Table III illustrates a number of different regions of the spectrum that provide prime candidate wavelengths for measuring glucose level in the blood. Specifically identified are: "Region A" which covers a spectrum range of approximately 1076 to 1086 nm; "Region B" which covers a spectrum range of approximately 809 to 823 nm; "Region C" which covers a spectrum range of approximately 693 to 701 nm; and "Region D" which covers a spectrum range of approximately 614 to 628 nm.

The above-identified wavelengths represent the midpoint wavelengths or the half-way point between the "A" and "B" wavelengths in Table III. In addition, Table III identifies other candidate mid-point wavelengths which are also practical. These wavelengths are identified as "other" and include: approximately 671 nm, approximately 782 nm, and approximately 1040 nm.

Figure 18C:
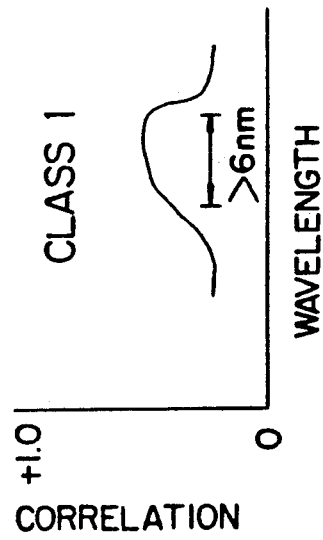
Figure 18D:
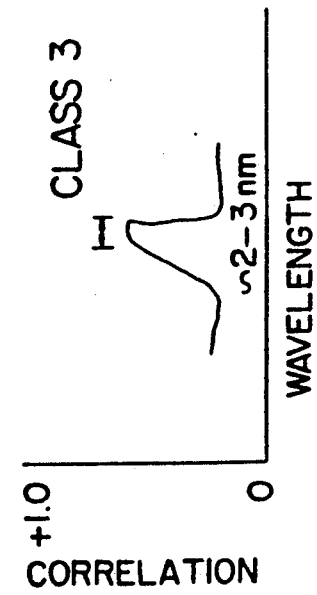

Further, the "class" column corresponds to the shape of the peak of the correlation versus wavelength curve as the "B" value in the numerator is varied. FIGS. 18A-D illustrate the classes of peaks which correspond to the shape of the correlation versus wavelength curve. FIG. 18A illustrates that in "Class 1", the log 1/I values are essentially insensitive to small wavelength errors which represents the ideal situation. FIG. 18B shows that the "Class 2" peak allows normal commercial tolerance on center wavelengths of optical filters (plus/minus 2 nanometers). FIG. 18C shows that the "Class 3" peak could require tighter than normal commercial tolerances on the center wavelength of the optical filters. A tolerance of approximately +/−1 nanometer would be required in this class. This tighter tolerance would increase the cost of such optical filters by perhaps a factor of two to four. FIG. 18D illustrates that in "Class 4", the measurement is hypersensitive to wavelength errors and would require the optical filter to provide a virtually correct wavelength. A small error would have a significant negative effect on measurement accuracy. The cost of providing such optical filters could be increased by a factor of ten over "Class 3" filters.

Denominator gaps described in Table III (i.e., D-E) are only representative values. As is customary in near-IR quantitative measurement, the denominator gaps can be increased substantially without undue impact on the total correlation coefficient. Thus, for convenience only, the denominator gaps of approximately ten nanometers have been shown in most cases.

In a preferred embodiment, the optimum wavelength candidates shown in Table III are A=771 nm, B=791 nm, D=1070 nm, and E=1080 nm. These wavelength candidates conform to the logical measurement regions defined above for Regions "J" and "K" which remove inaccuracies resulting from water absorption. Furthermore, these wavelengths provide for the highest correlation and allow use of lowest cost IRED's. In addition, these values have "Class 1" characteristics in that they are insensitive to small wavelength errors.

Table IV reproduced below presents the various candidates for the six wavelength model. The test data was derived in a similar fashion to the test data in Tables I and II. As would be expected, there are a smaller number of candidates for the six wavelength model compared to the four wavelength model. This is a direct result of the fundamental difference between the two algorithms. The six wavelength match uses second derivatives of the optical curve. The second derivative is only of value at the peak absorption points, whereas the first derivative algorithms have twice as many possible candidates since measurement can be made on either side of the peak absorption point.

TABLE IV $d^2OD/d^2OD$ for All Denomination, (D-E: E-F - 10)
(R > .8)
Criteria: Must be OK on 3 People, "$R_{min}$" is minimum for lowest person

| DEN "E" | $R_{Min}$ | "B" | GAP (A-B) & (B-C) | CLASS | DENOMINATOR GAP |
|---|---|---|---|---|---|
| 650 | .85 | 635 | 10 | 4 | 10 |
| 650 | .88 | 691 | 20 | 4 | 10 |
| 650 | .86 | 770 | 20 | 3 | 10 |
| 650 | .90 | 791 | 10 | 3 | 10 |
| 650 | .88 | 925 | 10 | 2 | 10 |
| 650 | .84 | 1000 | 20 | 2 | 10 |
| 650 | .86 | 1065 | 10 | 2 | 10 |
| 667 | .91 | 1065 | 40 | 2 | 40 |
| 667 | .90 | 791 | 30 | 2 | 30 |
| 687 | .94 | 825 | 20 | 1 | 50 |
| 820 | .92 | 667 | 40 | 2 | 10 |
| 824 | .94 | 667 | 20 | 2 | 30 |
| 844 | .94 | 667 | 30 | 1 | 10 |
| 883 | .92 | 667 | 30 | 3 | 10 |
| 910 | .87 | 667 | 30 | 4 | 10 |
| 920 | .85 | 656 | 30 | 3 | 10 |
| 920 | .87 | 667 | 40 | 3 | 10 |
| 930 | .90 | 667 | 40 | 2 | 10 |
| 940 | .88 | 667 | 40 | 3 | 10 |
| 950 | .82 | 791 | 30 | 2 | 10 |
| 960 | .90 | 667 | 40 | 3 | 10 |
| 970 | .88 | 667 | 40 | 3 | 10 |
| 980 | .88 | 667 | 40 | 3 | 10 |
| 980 | .85 | 825 | 20 | 3 | 10 |
| 990 | .85 | 667 | 30 | 3 | 10 |
| 1040 | .87 | 667 | 30 | 3 | 10 |
| 1050 | .83 | 667 | 30 | 3 | 10 |
| 1050 | .91 | 825 | 20 | 4 | 10 |
| 1060 | .88 | 667 | 30 | 4 | 10 |
| 1070 | .82 | 667 | 30 | 3 | 10 |
| 1080 | .83 | 788 | 20 | 2 | 10 |

Figure 20:
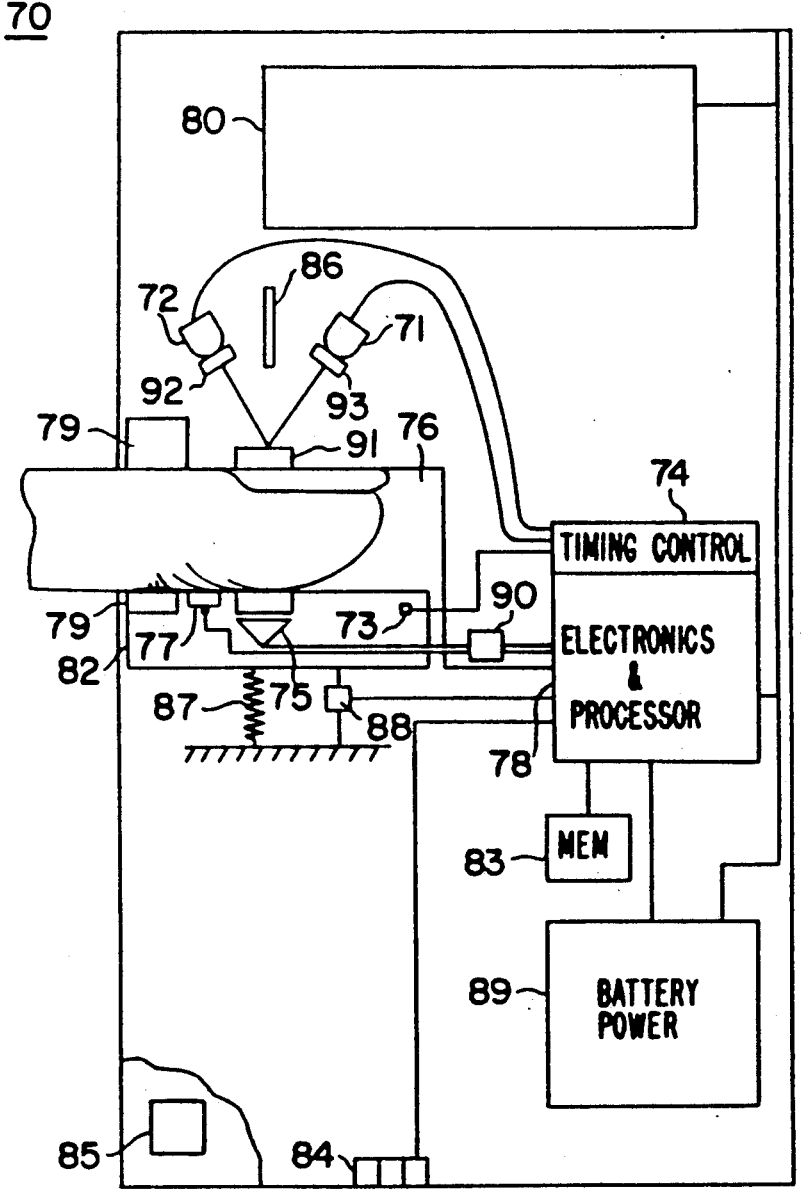
FIG. 20 illustrates a non-invasive glucose measurement instrument according to another embodiment of the present invention.

According to another embodiment of the present invention, FIG. 20 illustrates a non-invasive Self Monitoring Glucose Meter (NISMGM) 70 which is designed to measure blood glucose levels using near-IR transmission through the distal portion of the index finger. In this embodiment, the entire analytical instrument, including near-infrared point sources 71 and 72, transmitter, detector 75, amplifier 90, data processing circuitry 78, battery power source unit 89 and readout 80 is contained within a lightweight hand-held unit 70.

As illustrated in FIG. 20, the near-infrared point sources 71 and 72 separated by light baffle 86, are positioned so that near-infrared energy being emitted from the source will be directed through window 91 and onto the skin of the individual. The near-infrared point sources used in a preferred embodiment are IREDs. Further, optical filters 92 and 93 are between the IRED and the window 91 for filtering near-infrared radiation exiting each IRED and thereby allowing a narrow band of near-infrared radiation of predetermined wavelength to pass through.

In a preferred embodiment, the four wavelength model can be used with the following multiple linear regression algorithm:

$$C = K_0 = K_1 [\log 1/I_A - \log 1/I_B]/[\text{Log } 1/I_D - \text{Log } 1/I_E] + K_2 T_S + K_3 T_A$$

where $K_0$ through $K_3$ are the calibration constants described above, A, B, C and D are specific wavelengths where the optical data is being measured, $T_S$ is the local surface temperature of the finger in degrees centigrade divided by 100 and $T_A$ is the temperature of the air within the instrument in degrees centigrade divided by 100. Calibration constants k2 and k3 are independent regression terms.

In the embodiment shown in FIG. 20, any wavelength candidates may be chosen as described above which yield accurate glucose measurement levels. In a preferred embodiment, the wavelength candidates can be approximately A=771 nm, B=791 nm, C=1070 nm and D=1080 nm. The above wavelengths can be obtained using standard 880 nm IREDs including narrow band pass filters producing wavelengths at 770/790 nm, and standard 950 nm IREDs used at the 1070/1080 nm wavelengths. Also, IREDs having center wavelengths at longer wavelengths than 950 nm could be used as well.

In actual use, it is very important that the fingertip not be exposed to ambient light. Further, it is desirable that the actual measurement be made near the rear of the finger nail. FIG. 20 illustrates a Finger Sizer means 82 to securely position the user's finger inside the instrument and to provide sufficient blockage of ambient light. Spring 87 pushes the Finger Sizer 82 against the bottom of the individual's finger thereby providing a secure fit. Linear potentiometer 88 is connected to Finger Sizer 82 and can measure an individual's finger thickness. In addition, an inflatable diaphragm or foam iris (illustrated at 79) can be used to secure the individual's finger and shield light as well.

FIG. 20 further illustrates a measurement reading output device which is a large LCD display 80. Display 80 is advantageously constructed in a large size to facilitate reading by potential users who may have poor eyesight, one of the side effects of diabetes.

In a preferred embodiment, the NISMGM comprises means for displaying blood glucose level in two systems: the mg/dl for U.S. use and the mmol/L for Canadian use. Processor/controller 78 shown in FIG. 20 can perform this function. A change between the two display modes would typically only be required for initial setup. Thus, a slide type switch (not shown) positioned in a non-convenient place (e.g., in the battery compartment) could be used for this function.

FIG. 20 shows input/output connector 84 which allows the NISMGM to be connected to a "host instrument" which can determine the calibration constants for the instrument and transfer them automatically to the NISMGM. The input/output connector 84 could also be attached to an external keypad to allow manual entry of calibration constants.

The operation of the NISMGM is described as follows. Prior to making a finger measurement, a front panel push button 85 is pressed which provides for optical standardization which could be the "optical standard" derived from the empty chamber. This measurement would include a "dark correction," which can be a measurement with all IREDs off so that a light leak would be detected and automatically corrected.

FIG. 20 illustrates that when the finger is inserted into chamber 76, a built-in thermistor 77 measures the finger's temperature. The temperature measurement will be made at two times, approximately five seconds apart, and the actual temperature term $T_S$ being determined by using a logarithmic prediction equation as described in U.S. Pat. No. 4,286,376. Care should be taken that the finger holder 79 fit securely enough around the finger so as to block out light, and yet loose enough that pulse beating does not interfere with the measurement.

A second thermistor 73 is positioned inside the instrument for measuring the ambient temperature. The ambient temperature measurement could be measured at any time prior to the instrument's actual use, but preferably at the same time the optical standard is measured. No logarithmic prediction is needed for the optical measurement. Also, timing control means 74 in control circuitry 78 provides a battery protection feature which shuts off the instrument within approximately two minutes of the last measurement. No off button would be required.

In a further embodiment of the present invention, the NISMGM instrument comprises a memory unit 83 for storing a user's measurement data over a period of time. A built-in clock feature could also store the times at which the measurements were taken. The user would then be able to take the instrument to a doctor who could connect it to an output device, thereby dumping the information. This would allow the doctor to obtain information on the glucose level variability that occurred, for example, during the month.

Although the invention has been described in connection with certain preferred embodiments, it is not limited to them. Modifications within the scope of the following claims will be apparent to those skilled in the art. For example, accurate measurements can be obtained from parts of the body besides the wrist and the finger. The algorithm used to calculate blood constituent concentration(s) can be altered in accordance with known near-infrared analytical techniques.

We claim:

1. A near-infrared quantitative analysis instrument for non-invasive measurement of blood glucose in blood present in a body part of a subject, comprising:
   (a) introducing means including a near infrared energy source for introducing near-infrared energy into blood present in a body part of a subject wherein said introducing means introduces near-infrared energy of between about 600 and 1100 nanometers;
   (b) detecting means for detecting near-infrared energy emerging from the body part;
   (c) positioning means for positioning both the near-infrared introducing means and the detecting means closely adjacent to the body part; and
   (d) processing means for processing a first electrical signal produced by the detector means into a second signal indicative of the quantity of glucose present in the blood of the subject.

2. The analysis instrument of claim 1 wherein said introducing means includes a filter means for selectively transmitting near-infrared energy, said filter means being disposed between said source and said body part.

3. The analysis instrument of claim 2 wherein said filter means selectively transmits near-infrared energy of between about 600 and 1100 nanometers.

4. The analysis instrument of claim 3 wherein said filter means selectively transmits near-infrared energy of between about 780 and 810 nanometers and between about 1070 and 1090 nanometers.

5. The analytical instrument of claim 3 wherein said filter means selectively transmits near-infrared energy of between about 770 and about 795 nanometers and between about 1065 and about 1085 nanometers.

6. The analysis instrument of claim 1 wherein said instrument is a lightweight hand-held unit.

7. The analysis instrument of claim 6 wherein said body part is a finger of said subject.

8. The analysis instrument of claim 6 comprising a housing means for preventing said body part from being exposed to ambient light.

9. The analysis instrument of claim 8 wherein said housing means comprises a sizer means for securely positioning said body part in said housing means.

10. The analysis instrument of claim 8 wherein said housing means further comprises an inflatable diaphragm for shielding exposure to ambient light.

11. The analysis instrument of claim 8 wherein said housing means comprises a first section and second section connected together by a pivot means whereby said first section and said second section pivot relative to one another about a pivot axis of said pivot means.

12. The analysis instrument of claim 6 comprising a display means for displaying blood glucose level.

13. The analysis instrument of claim 12 wherein said display means can display blood glucose level expressed in mg/dl and mmol/L.

14. The analysis instrument of claim 6 further comprising an input/output means electrically connected to said processing means for inputting and outputting data from and to an outside instrument.

15. The analysis unit of claim 6 further comprising a memory means for storing measurement data.

16. The analysis unit of claim 15 wherein said memory means includes a clock means for storing times at which said measurement data is stored in said memory means.

17. The analysis instrument of claim 1 wherein the processing means processes the first signal according to the formula $$C = K_0 + K_1[\log 1/I_A - \log 1/I_B] + K_2 T_S$$

wherein C is concentration of glucose present in the blood, $K_0$ is an intercept constant, $K_1$ is the line slope of $$[\log 1/I_A - \log 1/I_B]$$

$K_2$ is a calibration constant, $\log 1/I_A$ and $\log 1/I_B$ each represent an optical density value at corresponding wavelengths A and B and $T_S$ represents the local surface temperature of said body part.

18. The analysis instrument of claim 1 wherein the signal processing means processes the first signal according to the formula $$C = K_0 + K_1[\log 1/I_A - 2 \cdot \log 1/I_B + \log 1/I_C] + K_2 T_1$$

wherein C is concentration of glucose present in the blood, $K_0$ is an intercept constant, $K_3$ is line slope of $$[\log 1/I_A - 2 \cdot \log 1/I_B + 1/I_C]$$

$K_2$ is a calibration constant, $\log 1/I_A$, $\log 1/I_B$, and $\log 1/I_C$ each represent an optical density value at corresponding wavelengths A, B and C, and $T_S$ represents the local surface temperature of said body part.

19. The analysis instrument of claim 1 wherein the signal processing means processes the signal according to the formula $$C = K_0 + K_1 \frac{[\log 1/I_A - \log 1/I_B]}{[\log 1/I_D - \log 1/I_E]} + K_2 T_S$$

wherein C is concentration of glucose present in the blood, $K_0$ is an intercept constant, $K_1$ is the line slope of $$\frac{[\log 1/I_A - \log 1/I_B]}{[\log 1/I_D - \log 1/I_E]}$$

$K_2$ is a calibration constant, $\log 1/I_A$, $\log 1/I_B$, $\log 1/I_D$ and $\log 1/I_K$ each represent an optical density value at corresponding wavelengths A, B, D and E and $T_S$ represents the local surface temperature of said body part.

20. The analysis instrument of claim 1 wherein the signal processing means processes the signal according to the formula $$C = K_0 + K_1 \frac{[\log 1/I_A - 2 \cdot \log 1/I_B + \log 1/I_C]}{[\log 1/I_D - 2 \cdot \log 1/I_E + \log 1/I_F]} + K_2 T_S$$

wherein C is concentration of glucose present in the blood, $K_0$ is an intercept constant, $K_1$ is the line slope of $$\frac{[\log 1/I_A - 2 \cdot \log 1/I_B + \log 1/I_C]}{[\log 1/I_D - 2 \cdot \log 1/I_E + \log 1/I_F]}$$

$K_2$ is a calibration constant, $\log 1/I_A$, $\log 1/I_B$, $\log 1/I_C$, $\log 1/I_D$, $\log 1/I_E$, and $\log 1/I_F$ each represent an optical density value at corresponding wavelengths A, B, C, D, E and F, and $T_S$ represents the local surface the temperature of said body part.

21. A non-invasive method for quantitatively analyzing blood glucose in blood of a subject, comprising:
  (a) introducing at least one pair of wavelengths of near-infrared energy from a near-infrared energy source into blood within a body part of the subject, said pair of wave lengths being within the range of about 600 to about 1100 nanometers;
  (b) detecting near-infrared energy emerging from the subject with a detector which provides a signal upon detecting energy emerging from the subject; and
  (c) processing the signal to provide a second signal indicative of the amount of glucose present in the body of the subject.

22. The method of claim 21 wherein said pair of wavelengths is centered on a wavelength within the range of about 600 to about 1100 nanometers.

23. The method of claim 21 wherein the first signal is processed according to the formula $$C = K_0 + K_1 [\log 1/I_A - \log 1/I_B] + K_2 T_S$$

wherein C is concentration of glucose present in the blood, $K_0$ is an intercept constant, $K_1$ is the line slope of $$[\log 1/I_A - \log 1/I_B]$$

$K_2$ is a calibration constant, $\log 1/I_A$ and $\log 1/I_B$ each represent an optical density value at corresponding wavelengths A and B and $T_S$ represents the local surface temperature of said body part.

24. The method of claim 21 wherein the first signal processing means processes the signal according to the formula $$C = K_0 + K_1 [\log 1/I_A - 2 \cdot \log 1/I_B + \log 1/I_C] + K_2 T_S$$

wherein C is concentration of glucose present in the blood, $K_0$ is an intercept constant, $K_1$ is line slope of $$[\log 1/I_A - 2 \cdot \log 1/I_B + 1/I_C]$$

$K_2$ is a calibration constant, $\log 1/I_A$, $\log 1/I_B$, and $\log 1/I_C$ each represent an optical density value at corresponding wavelengths A, B and C, and $T_S$ represents the local surface temperature of said body part.

25. The method of claim 21 wherein the signal processing means processes the signal according to the formula $$C = K_0 + K_1 \frac{[\log 1/I_A - \log 1/I_B]}{[\log 1/I_D - \log 1/I_E]} + K_2 T_S$$

wherein C is concentration of glucose present in the blood, $K_0$ is an intercept constant, $K_0$ is the line slope of $$\frac{[\log 1/I_A - \log 1/I_B]}{[\log 1/I_D - \log 1/I_E]}$$

$K_2$ is a calibration constant, $\log 1/I_A$, $\log 1/I_B$, $\log 1/I_D$ and $\log 1/I_E$ each represent an optical density value at corresponding wavelengths A, B, D and E and $T_S$ represents the local surface temperature of said body part.

26. The method of claim 21 wherein the first signal processing means processes the signal according to the formula $$C = K_0 + K_1 \frac{[\log 1/I_A - 2\cdot\log 1/I_B + \log 1/I_C]}{[\log 1/I_D - 2\cdot\log 1/I_E + \log 1/I_F]} + K_2 T_S$$

wherein C is concentration of glucose present in the blood, $K_0$ is an intercept constant, $K_1$ is the line slope of $$\frac{[\log 1/I_A - 2\cdot\log 1/I_B + \log 1/I_C]}{[\log 1/I_D - 2\cdot\log 1/I_E + \log 1/I_F]}$$

$K_2$ is a calibration constant, $\log 1/I_A$, $\log 1/I_B$, $\log 1/I_C$, $\log 1/I_D$, $\log 1/I_E$, and $\log 1/I_F$ each represent an optical density value at corresponding wavelengths A, B, C, D, E and F, and $T_S$ represents the local surface temperature of said body part.

27. The analysis instrument of claim 1 wherein the first signal processing means processes the signal according to the formula $$C = K_0 + K_1 \frac{[\log 1/I_A - \log 1/I_B]}{[\log 1/I_D - \log 1/I_E]} + K_2 T_S + K_3 T_A$$

wherein C is concentration of glucose present in the blood, $K_0$ is an intercept constant, $K_1$ is the line slope of $$\frac{[\log 1/I_A - \log 1/I_B]}{[\log 1/I_D - \log 1/I_E]}$$

$K_2$ and $K_3$ are calibration constants, $\log 1/I_A$, $\log 1/I_B$, $\log 1/I_D$ and $\log 1/I_E$ each represent an optical density value at corresponding wavelengths A, B, D and E, $T_S$ represents the local surface temperature of said body part and $T_A$ represents the ambient air temperature of said instrument.

28. The analysis instrument of claim 1 wherein the first signal processing means processes the signal according to the formula $$C = K_0 + K_1 \frac{[\log 1/I_A - 2\cdot\log 1/I_B + \log 1/I_C]}{[\log 1/I_D - 2\cdot\log 1/I_E + \log 1/I_F]} + K_2 T_S + K_3 T_A$$

wherein C is concentration of glucose present in the blood, $K_0$ is an intercept constant, $K_1$ is the line slope of $$\frac{[\log 1/I_A - 2\cdot\log 1/I_B + \log 1/I_C]}{[\log 1/I_D - 2\cdot\log 1/I_E + \log 1/I_F]}$$

$K_2$ and $K_3$ are calibration constants, $\log 1/I_A$, $\log 1/I_B$, $\log 1/I_C$, $\log 1/I_D$, $\log 1/I_E$, and $\log 1/I_F$ each represent an optical density value at corresponding wavelengths A, B, C, D, E and F, $T_S$ represents the local surface the temperature of said body part and $T_A$ represents the ambient temperature of said instrument.

29. The method of claim 21 wherein the first signal processing means processes the signal according to the formula $$C = K_0 + K_1 \frac{[\log 1/I_A - \log 1/I_B]}{[\log 1/I_D - \log 1/I_E]} + K_2 T_S + K_3 T_A$$

wherein C is concentration of glucose present in the blood, $K_0$ is an intercept constant, $K_1$ is the line slope of $$\frac{[\log 1/I_A - \log 1/I_B]}{[\log 1/I_D - \log 1/I_E]}$$

$K_2$ and $K_3$ are calibration constants, $\log 1/I_A$, $\log 1/I_B$, $\log 1/I_D$ and $\log 1/I_E$ each represent an optical density value at corresponding wavelengths A, B, D and E, $T_S$ represents the local surface temperature of said body part and $T_A$ represents the ambient temperature of said instrument.

30. The analysis instrument of any of claims 17-20, 27 or 28 wherein the corresponding wavelengths are between about 600 and about 1100 nanometers.

31. The analysis instrument of claim 30 wherein said corresponding wavelength A is between about 780 and about 810 nanometers and said corresponding wavelength B is between about 1070 and about 1090 nanometers.

32. The analysis instrument of claim 30 wherein said wavelength A is about 771 nanometers, said wavelength B is about 791 nanometers, said wavelength D is about 1070 nanometers, and said wavelength E is about 1080 nanometers.

33. The analysis instrument of claim 1 wherein said energy source comprises means for emitting near-infrared energy at a plurality of center wavelengths, said plurality of center wavelengths being separated by a constant wavelength, said introducing means further comprising control means for powering said energy source such that near-infrared energy at each said center wavelength is sequentially introduced into said body part.

34. The analysis instrument of claim 33 wherein said energy source comprises a plurality of infrared emitting diodes and wherein said control means sequentially powers each said plurality of infrared emitting diodes.

35. The analysis instrument of claim 33 further comprising means for identifying which two of said center wavelengths provide the a maximum difference when said subject is measured at a time of low glucose level and at a time of higher glucose level.

36. The analysis instrument of claim 33 wherein said constant wavelength is approximately 10 nanometers.

37. The analysis instrument of claim 17 wherein said energy source comprises a plurality of near-infrared emitting diodes.

38. The analysis instrument of claim 37 wherein said plurality of near-infrared emitting diodes comprises six near-infrared emitting diodes.

39. The analysis instrument of claim 37 wherein optical filters corresponding to optimum wavelength values for A and B for a given subject are installed in said instrument.

40. The method of claim 21 wherein said at least one pair of wavelengths is individually selected for a subject by the following:
    (a) sequentially introducing near-infrared energy into said body part of a subject at a plurality of center wavelengths, said plurality of center wavelengths being separated by a constant wavelength;
    (b) measuring a glucose level of said subject at a time of low glucose level and measuring a glucose of said subject level at a time of higher glucose level; and
    (c) determining from the measuring step which center wavelengths provide the maximum difference and using the determined wavelengths in subsequent measurements for said subject.

41. A near-infrared quantitative analysis instrument for non-invasive measurement of blood glucose levels in blood present in a body part of a subject, comprising:
    (a) introducing means including a near infrared energy source for introducing near-infrared energy of between about 600 to about 850 nanometers and between about 850 and 1100 nanometers into blood present in a body part of a subject;
    (b) detecting means for detecting near-infrared energy emerging from the body part; and
    (c) processing means for processing a first electrical signal produced by the detector means into a second signal indicative of the quantity of glucose present in the blood of the subject.

42. A near-infrared quantitative analysis instrument for non-invasive measurement of the concentration of a blood analyte in a body part of a subject comprising:
    (a) introducing means for introducing near-infrared energy into blood present in a body part of a subject wherein said introducing means introduces near-infrared energy of between about 600 and 1100 nanometers;
    (b) detecting means for detecting near-infrared energy emerging from the body part of the subject;
    (c) positioning means for positioning both the near-infrared introducing means and the detecting means closely adjacent to the body part; and
    (d) processing means for processing a first electrical signal produced by the detector means into a second signal indicative of the analyte concentration in the blood of the subject.

43. A non-invasive method for quantitatively analyzing the concentration of a blood analyte in a body part of a subject, comprising:
    (a) introducing near-infrared energy from a near-infrared energy source into blood within a body part of the subject, said near-infrared energy being within the range of about 600 to about 1100 nanometers;
    (b) detecting near-infrared energy emerging from the subject with a detector which provides a signal upon detecting energy emerging from the subject; and
    (c) processing the signal to provide a second signal indicative of the analyte concentration in the blood of said subject.

* * * * *

UNITED STATES PATENT AND TRADEMARK OFFICE
CERTIFICATE OF CORRECTION

PATENT NO. : 5,086,229
DATED : February 4, 1992
INVENTOR(S) : R. D. Rosenthal et al.

It is certified that error appears in the above-identified patent and that said Letters Patent is hereby corrected as shown below:

ON THE TITLE PAGE:

Item [*], Notice: "July 2, 1991" should be --July 2, 2008--.

Col. 9, line 37 "K" should be --$K_1$--.

Col. 21, line 55 (claim 19) "$1/I_k$" should be --$1/I_E$--.

Col. 22, line 67 (claim 25) "$K_o$" (second occurrence) should be --$K_1$--.

Signed and Sealed this

Twenty-first Day of September, 1993

*Attest:*

BRUCE LEHMAN

*Attesting Officer*     *Commissioner of Patents and Trademarks*